United States Patent
Schoenberg

(10) Patent No.: US 7,590,550 B2
(45) Date of Patent: Sep. 15, 2009

(54) CONNECTING CONSUMERS WITH SERVICE PROVIDERS

(75) Inventor: Roy Schoenberg, Boston, MA (US)

(73) Assignee: American Well Inc., Boston, MA (US)

( * ) Notice: Subject to any disclaimer, the term of this patent is extended or adjusted under 35 U.S.C. 154(b) by 175 days.

(21) Appl. No.: 11/763,680

(22) Filed: Jun. 15, 2007

(65) Prior Publication Data
US 2008/0065726 A1 Mar. 13, 2008

Related U.S. Application Data

(60) Provisional application No. 60/829,139, filed on Oct. 11, 2006, provisional application No. 60/829,140, filed on Oct. 11, 2006, provisional application No. 60/828,921, filed on Oct. 10, 2006, provisional application No. 60/828,924, filed on Oct. 10, 2006, provisional application No. 60/824,966, filed on Sep. 8, 2006.

(51) Int. Cl.
  G06Q 10/00 (2006.01)
  G06Q 50/00 (2006.01)
  G06Q 99/00 (2006.01)
  A61B 5/00 (2006.01)
  G06F 19/00 (2006.01)

(52) U.S. Cl. .................. 705/2; 705/3; 705/52
(58) Field of Classification Search .......... 705/2, 705/3, 4
See application file for complete search history.

(56) References Cited

U.S. PATENT DOCUMENTS

| | | | |
|---|---|---|---|
| 5,801,755 A | 9/1998 | Echerer | 348/13 |
| 5,995,939 A | 11/1999 | Berman et al. | |
| 6,151,581 A * | 11/2000 | Kraftson et al. | 705/3 |
| 6,322,502 B1 | 11/2001 | Schoenberg et al. | |
| 6,381,576 B1 * | 4/2002 | Gilbert | 705/2 |
| 6,463,417 B1 | 10/2002 | Schoenberg | |
| 6,735,569 B1 * | 5/2004 | Wizig | 705/4 |
| 7,478,049 B2 | 1/2006 | Schoenberg | |
| 7,172,120 B2 | 2/2007 | Schoenberg | |
| 2003/0023508 A1 | 1/2003 | Deep | |

(Continued)

FOREIGN PATENT DOCUMENTS

WO   WO 00/57326   9/2000

(Continued)

OTHER PUBLICATIONS

Notification of Transmittal of the International Search Report and The Written Opinion of the International Searching Authority, Or the Declaration dated Jan. 28, 2008, (11 pages).

(Continued)

*Primary Examiner*—Gerald J. O'Connor
*Assistant Examiner*—Amber L Altschul
(74) *Attorney, Agent, or Firm*—Fish & Richardson P.C.

(57) ABSTRACT

A request is received from a consumer of services to consult with a service provider having a service provider profile that satisfies at least some attributes in a set of attributes that define a suitable service provider; an available service provider satisfying at least some of the attributes in the set of attributes is identified; and a communication channel is provided to establish a communication between the consumer of services and the identified service provider.

30 Claims, 15 Drawing Sheets

U.S. PATENT DOCUMENTS

| | | | |
|---|---|---|---|
| 2003/0093294 A1 | 5/2003 | Passantino | 705/2 |
| 2003/0144580 A1 | 7/2003 | Iliff | 600/300 |
| 2003/0195838 A1 | 10/2003 | Henley | |
| 2004/0019579 A1* | 1/2004 | Herz et al. | 707/1 |
| 2004/0111297 A1 | 6/2004 | Schoenberg | |
| 2004/0111298 A1 | 6/2004 | Schoenberg | |
| 2004/0111622 A1 | 6/2004 | Schoenberg | |
| 2004/0152952 A1 | 8/2004 | Gotlib et al. | |
| 2004/0153343 A1 | 8/2004 | Gotlib et al. | |
| 2004/0181430 A1 | 9/2004 | Fotsch et al. | 705/2 |
| 2005/0065813 A1 | 3/2005 | Mishelevich et al. | 705/2 |
| 2005/0108052 A1 | 5/2005 | Omaboe | 705/2 |
| 2005/0125252 A1 | 6/2005 | Schoenberg | |
| 2005/0125254 A1 | 6/2005 | Schoenberg | |
| 2005/0125435 A1 | 6/2005 | Schoenberg | |
| 2005/0125446 A1 | 6/2005 | Schoenberg | |
| 2005/0125487 A1 | 6/2005 | O'Connor et al. | |
| 2005/0182743 A1 | 8/2005 | Koenig | 707/1 |
| 2005/0234739 A1 | 10/2005 | Schoenberg | |
| 2005/0234745 A1 | 10/2005 | Schoenberg | |
| 2005/0288965 A1 | 12/2005 | Van Eaton et al. | 705/2 |
| 2006/0106644 A1* | 5/2006 | Koo et al. | 705/3 |
| 2006/0116900 A1 | 6/2006 | Jensen | |
| 2006/0122850 A1 | 6/2006 | Ward et al. | |
| 2006/0136264 A1 | 6/2006 | Eaton et al. | |
| 2006/0161457 A1 | 7/2006 | Rapaport et al. | 705/2 |
| 2006/0247968 A1 | 11/2006 | Kadry | |
| 2007/0088580 A1 | 4/2007 | Richards, Jr. | |
| 2007/0150372 A1 | 6/2007 | Schoenberg | |
| 2008/0065414 A1 | 3/2008 | Schoenberg | |
| 2008/0133511 A1 | 6/2008 | Schoenberg | |
| 2009/0063188 A1 | 3/2009 | Schoenberg | |
| 2009/0089074 A1 | 4/2009 | Schoenberg | |
| 2009/0089084 A1 | 4/2009 | Schoenberg | |
| 2009/0089085 A1 | 4/2009 | Schoenberg | |
| 2009/0089086 A1 | 4/2009 | Schoenberg | |
| 2009/0089088 A1 | 4/2009 | Schoenberg | |
| 2009/0089090 A1 | 4/2009 | Schoenberg | |
| 2009/0089096 A1 | 4/2009 | Schoenberg | |
| 2009/0089097 A1 | 4/2009 | Schoenberg | |
| 2009/0089098 A1 | 4/2009 | Schoenberg | |
| 2009/0089147 A1 | 4/2009 | Schoenberg | |

FOREIGN PATENT DOCUMENTS

| | | |
|---|---|---|
| WO | WO 01/22718 | 3/2001 |

OTHER PUBLICATIONS

Notification of Transmittal of The International Search Report and The Written Opinion dated Jan. 28, 2008, (9 pages).
U.S. Appl. No. 12/031,018, filed Feb. 14, 2008, Schoenberg.
U.S. Appl. No. 12/264,524, filed Nov. 4, 2008, Schoenberg.
U.S. Appl. No. 12/038,110, filed Feb. 27, 2008, Schoenberg.
U.S. Appl. No. 12/061,338, filed Apr. 2, 2008, Schoenberg.
U.S. Appl. No. 12/098,669, filed Apr. 7, 2008, Schoenberg.
U.S. Appl. No. 12/117,324, filed May 8, 2008, Schoenberg.
U.S. Appl. No. 12/059,165, filed Mar. 31, 2008, Schoenberg.
U.S. Appl. No. 12/034,797, filed Feb. 21, 2008, Schoenberg.
U.S. Appl. No. 12/129,172, filed May 29, 2008, Schoenberg.
U.S. Appl. No. 12/098,720, filed Apr. 7, 2008, Schoenberg.
U.S. Appl. No. 12/256,216, filed Oct. 22, 2008, Schoenberg.
U.S. Appl. No. 12/098,758, filed Apr. 7, 2008, Schoenberg.
U.S. Appl. No. 12/124,247, filed May 21, 2008, Schoenberg.
U.S. Appl. No. 12/059,292, filed Mar. 31, 2008, Schoenberg.
U.S. Appl. No. 12/140,760, filed Jun. 17, 2008, Schoenberg.
U.S. Appl. No. 12/105,784, filed Apr. 18, 2008, Schoenberg.
U.S. Appl. No. 12/098,732, filed Apr. 7, 2008, Schoenberg.
Office Action, dated Jan. 9, 2008, issued in related U.S. Appl. No. 11/763,700.
Final Office Action, dated Oct. 7, 2008, issued in related U.S. Appl. No. 11/763,700.
Office Action, dated Feb. 6, 2009, issued in related U.S. Appl.No. 12/031,018.
Office Action, dated Jan. 9, 2009, issued in related U.S. Appl. No. 11/763,700.

* cited by examiner

⊕ CareTalks | Home | My Agenda | My Health | Message Center | E-Nurse | Provider Search | Help

My Agenda

To-Do List

Upcoming Appointments ▽

| S | M | T | W | T | F | S |
|---|---|---|---|---|---|---|
|   |   | MAY | 2007 |   |   |   |
| 29 | 30 | 1 | 2 | 3 | 4 | 5 |
| 6 | 7 | [8] | 9 | 10 | 11 | 12 |
| 13 | 14 | 15 | 16 | 17 | 18 | 19 |
| 20 | 21 | 22 | 23 | 24 | 25 | 26 |
| 27 | 28 | 29 | 30 | 31 | 1 | 2 |

📅 5/10/07 at 4:30 pm EST with Dr. John Kravitz

📅 5/22/07 at 8:00 am EST with Dr. Danielle Thompson

📅 6/7/07 at 2:45 pm EST with Nurse Kelly Connors

Waiting Room

You are waiting for ....

👤 Dr. John Kravitz [will timeout at 12:25pm]

Past Engagements

---

TO DO LIST — 298

📝 Conversation with an OBGYN                                      ✗ Delete

TOPICS: [Added by Self - 3/21/07]
Irregular Menstruation: I have irregular menstruation. Painful cycle. N...
Conducting Breast Self-Exams: Would like training on breast self-exa...
Mammography: Would like to know more about Mammography and its i...

[Added by Dr. Robert Smith - 3/20/07]
Mirum est Notare Quam: Invesigationes demonstraverunt lectore ame...
Claram Anteposuerit: Nam liber tempor cum soluta claritatem nonoum...

CONNECT:
⇨ First Available
🔍 Find a Provider
✚ Add Topic

📝 Conversation with a Dermatologist                               ✗ Delete

TOPICS: [Added by Dr. Robert Smith - 3/20/07]
Mirum est Notare Quam: Invesigationes demonstraverunt lectore ame...
Claram Anteposuerit: Nam liber tempor cum soluta claritatem nonoum...
Fiant Sollemnes in Futurum: Dolore magna clarit aliquam erat volutpa...

CONNECT:
⇨ First Available
🔍 Find a Provider
✚ Add Topic

▶ Video: Beginning an Exercise Regimen

[Added by eNurse - 3/15/07]
This new body-shaping workout is aimed at "beginners of all ages,"
especially those who have never lifted weights. The program design here is
simple, easy to follow and guaranteed to get you started on the right track.

OPTIONS:
▶ Watch Video

📊 Tracker: Monthly Glucose Level (Reoccurring)                    ✗ Delete

[Added by eNurse - 3/15/07]
This new body-shaping workout is aimed at "beginners of all ages,"
especially those who have never lifted weights. The program design here is
simple, easy to follow and guaranteed to get you started on the right track.

OPTIONS:
📈 Launch Tracker

↙ 340

| Criteria | Example | Impact on engagement cost |
| --- | --- | --- |
| Provider type | See below | Yes |
| Provider Gender | Male, female | No |
| Years of practice | 2, 20 | No |
| Graduation school | Tufts University Medical School | No |
| Board Certification | Yes/No | Yes |
| Professional Specialty | Cardiology, Pediatrics, ObGyn | No |
| Academic Appointment | Associate Professor, Harvard Medical School | No |
| Country of Residence | US, UK, India | Yes |
| Language | List of languages | No |
| Demographics | Zip code, city, state | No |
| Licensed to prescribe medications | List of states | Yes |
| Provider Contract | A list of health plan products the provider is associated with ("in network") | Yes |

FIG. 9

CONNECTING CONSUMERS WITH SERVICE PROVIDERS

CLAIM OF PRIORITY

This application claims priority under 35 USC §119(e) to provisional U.S. Patent Application 60/824,966, filed on Sep. 8, 2006, 60/828,921, filed Oct. 10, 2006, 60/828,924, filed Oct. 10, 2006, 60/829,139, filed Oct. 11, 2006, and 60/829,140, filed Oct. 11, 2006, the entire contents of which are hereby incorporated by reference.

BACKGROUND

The present disclosure is directed to connecting consumers with service providers.

Systems have been developed to connect consumers and their providers over the Internet and the World Wide Web. Some systems use e-mail messaging and web-based forms to increase the level of connectivity between a member of a health plan and his assigned health care provider. The consumer sends an e-mail or goes to a website that generates and sends a message (typically an e-mail or an e-mail type message) to a local provider.

These types of services have been broadly referred to as "e-visits." While generally viewed as an addition to the spectrum of services that may be desired by consumers, the benefits of such services are not clear. One of the concerns associated with offering additional communication channels, such as e-mail, is that it can result in over consumption of services, rather than provide for better coordination.

Until recently, the notion of an electronic encounter was not even coded in the standard financial coding schemes used for submitting medical claims, preventing proper reimbursement of providers for such encounters. This gap has been recently corrected by the introduction of CPT (current procedural terminology) code 0074T, allowing providers to submit a reimbursement claim for an electronic encounter (e.g., e-visit) with their patients. Most plans at this time, however, do not include this service code as a covered service (i.e., a benefit) making it an out-of-pocket expense for members and an unattractive offering for providers (who need to charge members directly for such encounters).

Recently, a number of health plans announced their intention to begin remunerating providers for electronic visits (i.e., paying a certain consideration for claims submitted with a CPT 0074T code). While limited to pilot projects, plans are embracing the notion of consumerism by offering advanced tools for consumers to become informed and acquire medical services. Facilitating timely and more organized communication between the member and their provider is perceived as a natural investment in the new consumer-driven healthcare world. While still at an early stage, interest in e-visits has picked up both in the commercial world as well as in the strategic planning sessions of health plans around the country. Vendors offering health portals for health plans typically now describe their roadmap for the incorporation (or interfacing with) e-visit platforms.

SUMMARY

In general, in one aspect, a request is received from a consumer of services to consult with a service provider having a service provider profile that satisfies at least some attributes in a set of attributes that define a suitable service provider, an available service provider satisfying at least some of the attributes in the set of attributes is identified, and a communication channel is provided to establish a communication between the consumer of services and the identified service provider.

Implementations may include one or more of the following features.

Identifying the available service provider includes monitoring availability of the identified service provider. also including activating the communication channel when the identified service provider becomes available. Identifying the available service provider includes identifying a set of service providers, each service provider having a profile matching at least some of the attributes, monitoring availability of the matching service providers, and when one of the matching service providers becomes available, initiating real-time communication between the available service provider and the consumer of services. The identified service provider is of a first type of service provider, a second available service provider of a second type of service provider satisfying at least some of the attributes in the set of attributes is identified, and a second real-time communication channel for a communication between the consumer of services and the second identified service provider is provided. The communication channel for whichever identified service provider is available first is provided first.

If the communication channel with the first identified service provider is provided before the second communication channel, information describing an outcome of the communication between the consumer of services and the first identified service provider is provided to the second identified service provider in advance of providing the second communication channel. Information describing an outcome of the communication between the consumer of services and the identified service provider is provided to a second service provider associated with the consumer of services.

Providing the communication channel includes identifying a communication method for contacting the consumer of services and instructing the identified service provider to initiate a communication using the identified method. Providing the communication channel includes initiating a first communication channel with the consumer of services, initiating a second communication channel with the identified service provider, and connecting the first and second communication channels. Identifying the available service provider includes receiving an indication that a service provider satisfying at least some of the attributes in the set of attributes has initiated a first communication channel. Providing the real-time communication channel includes initiating a second communication channel with the consumer of services and connecting the first and second communication channels.

In general, in one aspect, indications that members of a pool of service providers have become available are received, a request is received from a consumer of services to consult with a service provider, an available member of the pool is identified, and a real-time communication is initiated between the consumer of services and the identified member of the pool. In some implementations, the request includes an identification of a time in the future, and identifying the member of the pool and initiating the communication take place at the identified time.

In general, in one aspect, a request is received from a patient for an on-demand, real-time consultation with a physician, at least one available physician with whom the patient should consult is identified, and a communication channel is activated between the patient and the available physician to allow the requested consultation.

Implementations may include one or more of the following features.

Identifying the available physician includes identifying at least one type of physician with whom the patient should consult, identifying a set of physicians of the identified type, determining the current availability of physicians in the identified set, and identifying an available physician in the identified set. The patient is associated with a primary physician, and identifying the set of physicians includes identifying physicians other than the patient's primary physician. Information describing an outcome of the consultation is provided to the patient's primary physican.

In general, in one aspect, a request is sent from a patient for an on-demand, real-time consultation with a physician, a message is received identifying at least one available physician with whom the patient should consult, and a connection is made to a communication channel established between the patient and the available physician to allow the requested consultation.

BRIEF DESCRIPTION OF THE FIGURES

FIGS. 2A, 5A-5D, 7, 8, and 10 are screen images of a user interface for an engagement brokerage service.

FIG. 9 is a table of sample criteria used in an engagement brokerage system.

DETAILED DESCRIPTION

Overview

The system described below provides an integrated information and communication platform that enables consumers of services to identify and prioritize service providers with whom they should consult and to carry out consultations with such service providers in an efficient manner. Consumers are able to consult on-line with an expert service provider, at a mutually convenient time and place, even when the two parties are geographically separated. This integrated platform is referred to herein as an engagement brokerage service (brokerage).

Figure 1:
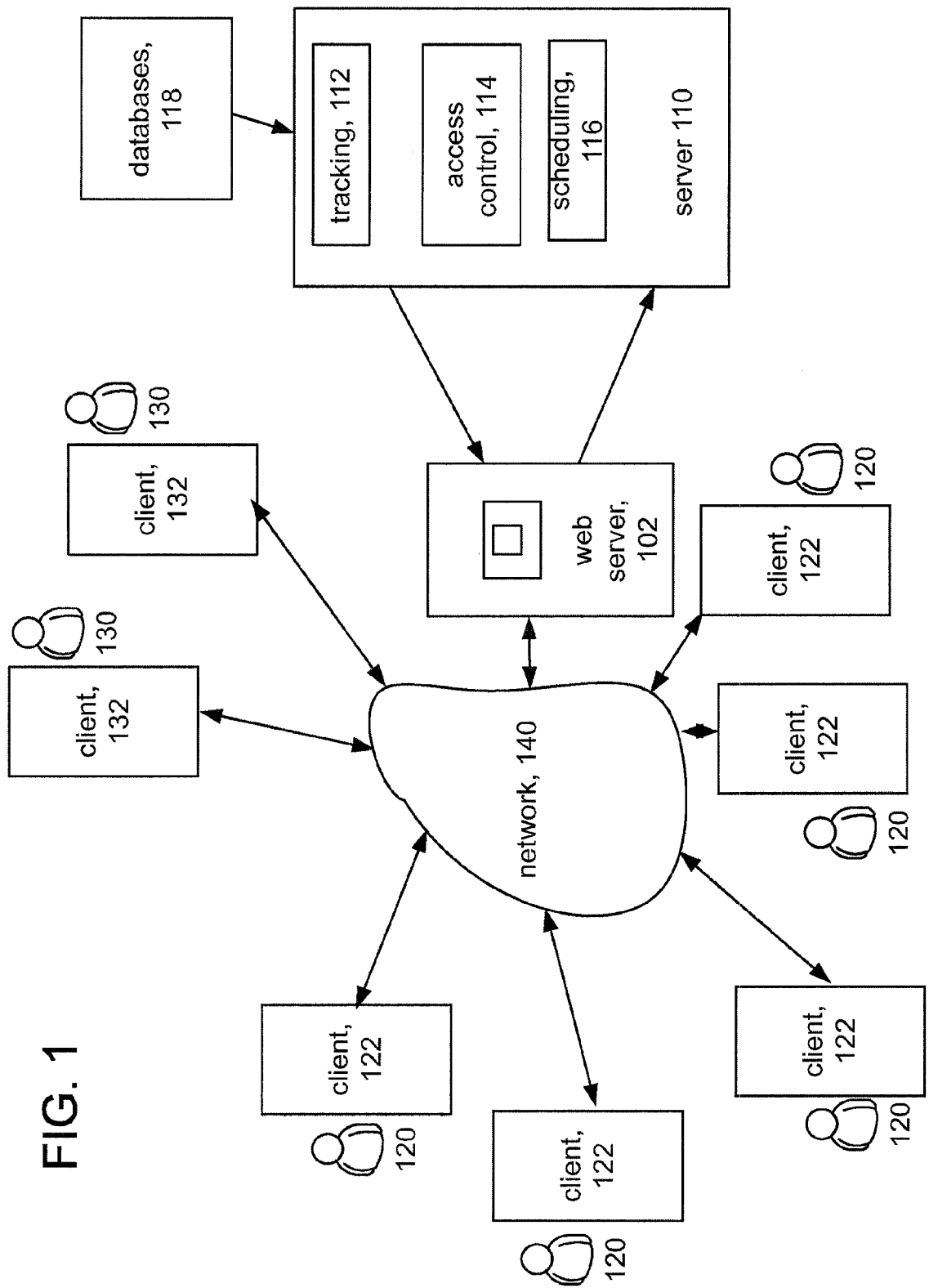
FIG. 1 is a diagrammatic view of an engagement brokerage service.

FIG. 1 shows an example system 100 implementing the brokerage service. The system 100 includes a computerized system or server 110 for making connections between consumers 120, at client systems 122, and service providers 130, at client systems 132, over a network 140, e.g., the Internet or other types of networks. The computerized system 110 may operate as a service running on a web server 102.

The computerized system 110 includes an availability or presence tracking module 112 for tracking the availability of the service providers 130. Availability or presence is tracked actively or passively. In an active system, one or more of the service providers 130 provides an indication to the computerized system 110 that the one or more service providers are available to be contacted by consumers 120 and an indication of the mode by which the provider may be contacted. In some examples of an active system, the provider's computer, phone, or other terminal device periodically provides an indication of the provider's availability (e.g., available, online, idle, busy) to the system 110 and a mode (e.g., text, voice, video, etc.) by which he can be engaged. In a passive system, the computerized system 110 presumes that the service provider 130 is available by the service provider's actions, including connecting to the computerized system 110 or registering the provider's local phone number with the system. In some examples of a passive system, the system 110 indicates the provider 130 to be available at all times until the provider logs off, except when the provider is actively engaged with a consumer 120.

The computerized system 110 also includes one or more processes such as the tracking module 112 and a scheduling module 116. The system 110 accesses one or more databases 118. The components of the system 110 and the web server 102 may be integrated or distributed in various combinations as is commonly known in the art.

Using the system 100, a consumer 120 communicates with a provider 130. The consumers 120 and providers 130 connect to the computerized system 110 through a website or other interface on the web server 102 using client devices 122 and 132, respectively. Client devices 122 and 132 can be any combination of, e.g., personal digital assistants, land-line telephones, cell phones, computer systems, media-player-type devices, and so forth. The client devices 122 and 132 enable the consumers 120 to input and receive information as well as to communicate via video, audio, and/or text with the providers 130.

Limited by office hours and other patients, providers struggle with the idea of adding another service commitment to their existing workload. Patients sending queries to their providers can not expect an immediate response and are often asked to schedule an appointment for further evaluation. Providers are, however, often available at times that are not convenient for their patients, for example, in the event of a last-minute cancellation. Providers also may be available for e-visits during otherwise idle times, such as when home, during their commute, and so forth. The brokerage supplements existing provider availability to allow whichever providers are available at any given time to provide e-Visits to whichever consumers need a consultation at that time. Instead of relying on the unlikely availability of a specific provider for any given consumer, the brokerage connects the consumer to all online providers capable of addressing the consumer's needs. The brokerage has distinct features including the ability to engage in live communication with a suitable, selectable provider and the ability to do so on-demand.

One advantage that the brokerage provides is that the brokerage constantly monitors the availability of a provider for an engagement and thus, consumers receive immediate attention to address their questions or concerns, since the brokerage will connect them to available service providers. In order to achieve such a level of availability, the system assimilates the discretionary or fractional availability windows of time offered by individual providers into a continuous availability perception by consumers. Since many of the services offered to consumers are on-demand, consumers have little expectation that the same provider will be constantly available, rather, they expect that some provider will be available.

The computerized system 110 provides information and services to the consumers 120 in addition to connecting them with providers 130. The computerized system 110 includes an access control facility 114, which manages and controls whether a given consumer 120 may access the system 110 and what level or scope of access to the features, functions, and services the system 110 will provide.

The consumer 120 use the system 100 to find out more information about a topic of interest or, for example, a potential medical condition. The computerized system 110 identifies service providers 130 that are available at any given moment to communicate with a consumer about a particular product, service, or related topic or subject, for example, a medical condition. The computerized system 110 facilitates communication between the consumer 120 and provider 130, enabling them to communicate, for example, via a data-network-facilitated video or voice communication channel (such as Voice over IP), land and mobile telephone network channels, and instant messaging or chat. In some examples, the availability of one or more providers 130 is tracked, and at the instant a consumer 120 desires to connect and communicate with a provider, the system 110 determines whether a provider is available. If a particular provider 130 is available, the system 110 assesses the various modes of communication that are available and connects the consumer 120 and the provider 130 through one or more common modes of communication.

The system selects a mode of communication to use based in part on the relative utility of the various modes. The preferred mode for an engagement is for both the consumer 120 and the provider 130 to use web-based consoles, as this allows each of the other modes to be used as needed. For example, consumers and providers may launch chat sessions, voice calls, or video chats from within a web-based console like that shown in FIG. 2A, below. A web based console also provides on-demand access to records, such as the consumer's medical history, and other information. If only one of the participants in an engagement has access to a web console, the system 110 connects that participant's console to whatever form of communication the other party has available. For example, if the consumer is on the phone and the provider is using a web browser, the system 110 may connect the consumer's phone call to a VoIP session that the provider can access through the web.

If the provider 130 is not available, the system 110 identifies other available providers 130 that would meet the consumer 120's needs. The system 110 enables the consumer 120 to send a message to the consumer's chosen provider. The consumer can also have the system 110 contact the consumer in the future when the chosen provider is available.

By way of illustration, the system 100 connects members of healthcare plans with providers of healthcare products and services. For example, the service providers 130 may be physicians, and the service consumers 120 may be patients. The service providers and service consumers may also be lawyers and clients, contractors and homeowners, or any other combination of a provider of services and a consumer of services.

The system enables the consumer to search for providers that are available at the time the consumer is searching and enables the consumer to engage a provider on a transactional basis or for a one-time consultation. A consumer is able to engage a world-renowned specialist for a consultation or second opinion, even though the specialist is located too far away from the consumer to become a regular client, patient, or consumer. The consumer can use that specialist's advice when considering services by a local service provider. For example, a patient in a suburban town with a rare condition may consult with a specialist in a distant city, and then, based on that consultation, select a local physician for treatment.

Figure 2A:
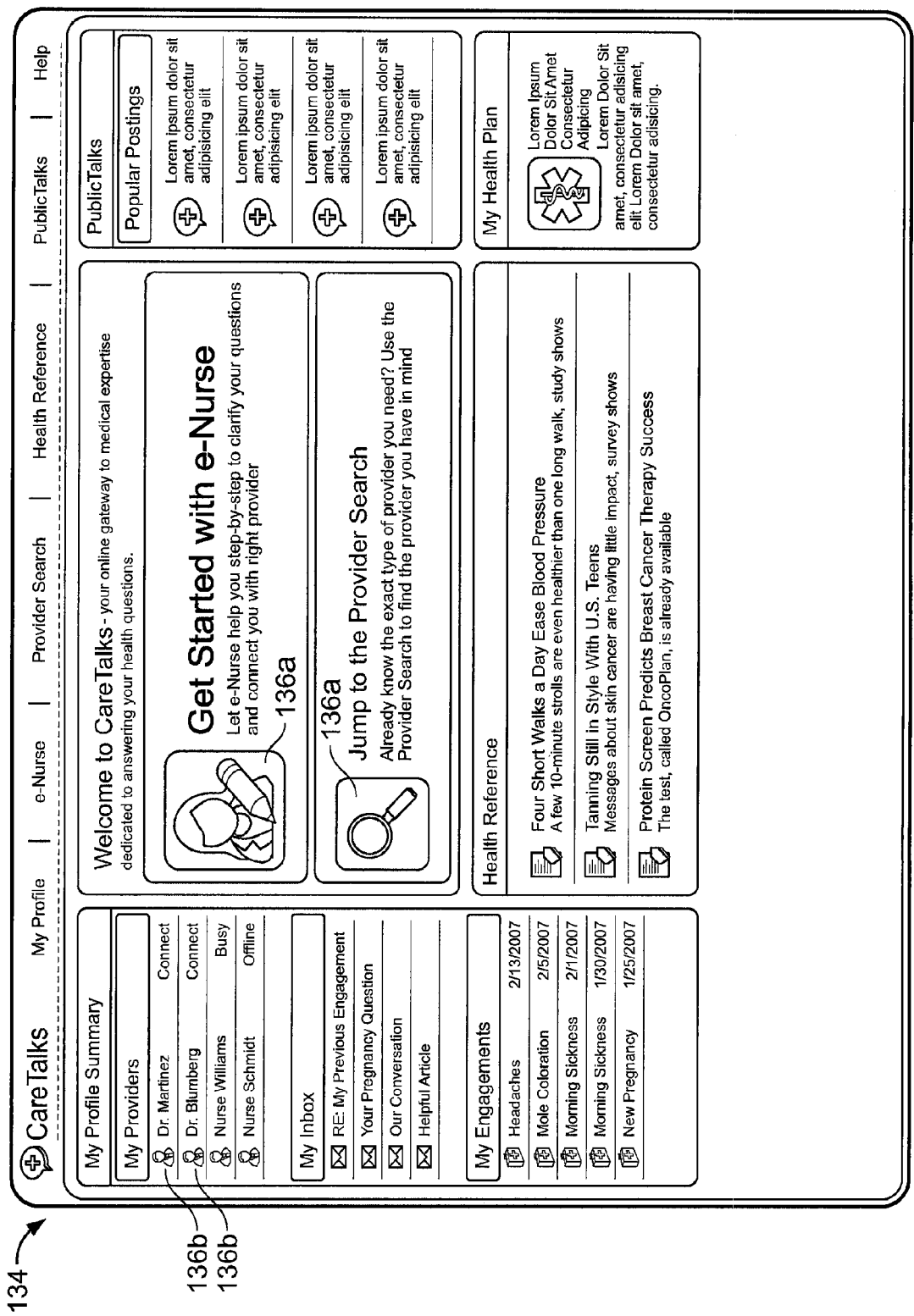
Figure 10:
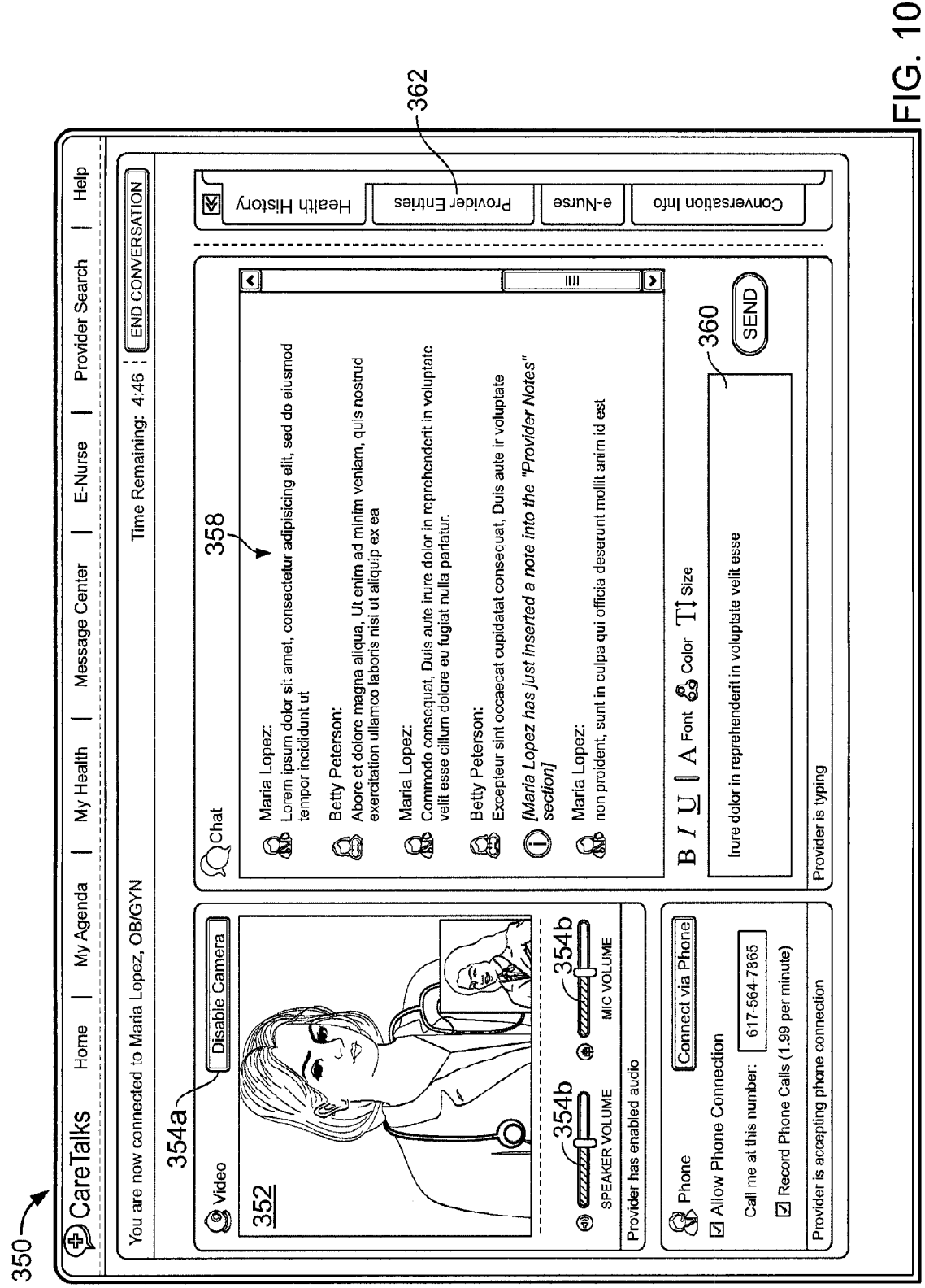

FIG. 2A shows a page 134 of the main user interface to the brokerage. Many of the web-based functions are also provided by an Interactive Voice Response (IVR) system, as discussed below. As noted the server 110 sends web pages like the page 134 to the consumer 120 and the provider 130 and receives responses from the consumer 120 and the provider 130. In some examples, the application server provides a predefined sequence of web pages or voice prompts to the consumer 120 or the provider 130. FIG. 2 shows an interface intended for the consumer 120. A similar interface is provided for providers 130, as shown in FIG. 10.

The web page 134 includes various elements to enable the consumer 120 (to input information. These interface elements include buttons 136a and text 136b to enable the consumer 120 to select information and to navigate the website Other standard elements (not shown) can include text boxes to receive textual information and menus (such as drop-down menus) to enable the consumer 120 to select information from a menu or list.

Figure 2B:
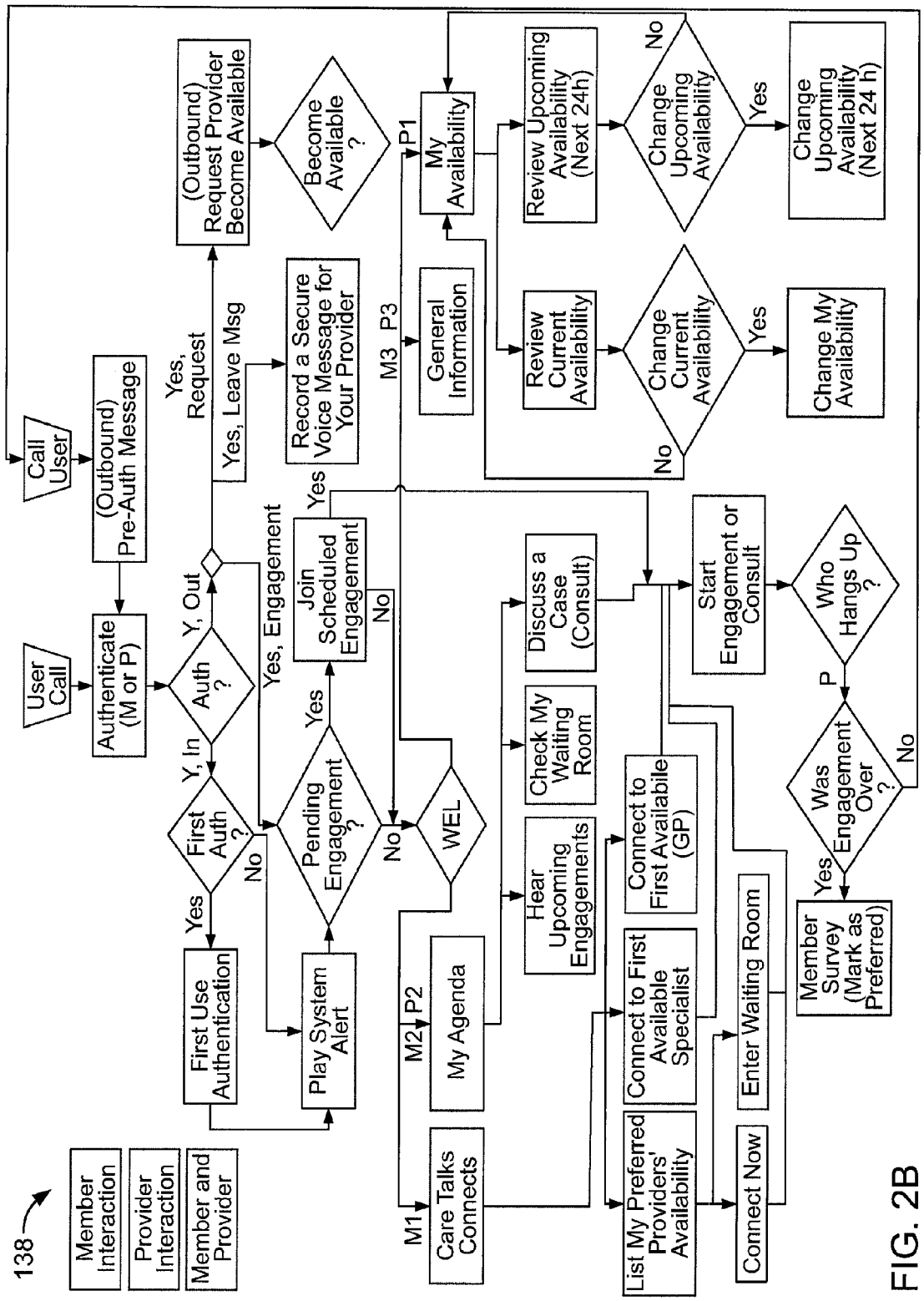
FIG. 2B is a flow chart for an interactive voice response system interface for an engagement brokerage service.

Referring now to FIG. 2B, an example of logic for use in an IVR system is shown. It is not intended that FIG. 2B be described in detail, since it is one of many possible logic flows for such a system and the exact details on questions and sequences is not important to an understanding of the concepts disclosed herein. In the IVR system, the voice prompts include questions or statements that elicit information from the consumer 120 and the provider 130 as shown. The consumer 120 and the provider 130 input information by speaking into the microphone of the telephone or other terminal device and their speech is stored as received or converted to text using voice recognition. In some examples, the questions are multiple choice questions and the consumer 120 or the provider 130 responds with spoken responses or by pressing buttons on the keypad of their phone or other terminal device. The IVR system follows a series of flow charts like the flowchart 138 in FIG. 2B and can include a menu system, in which case the consumer 120 or provider 130 moves forward or backward, or exits the system by pressing certain keys.

Figure 3:
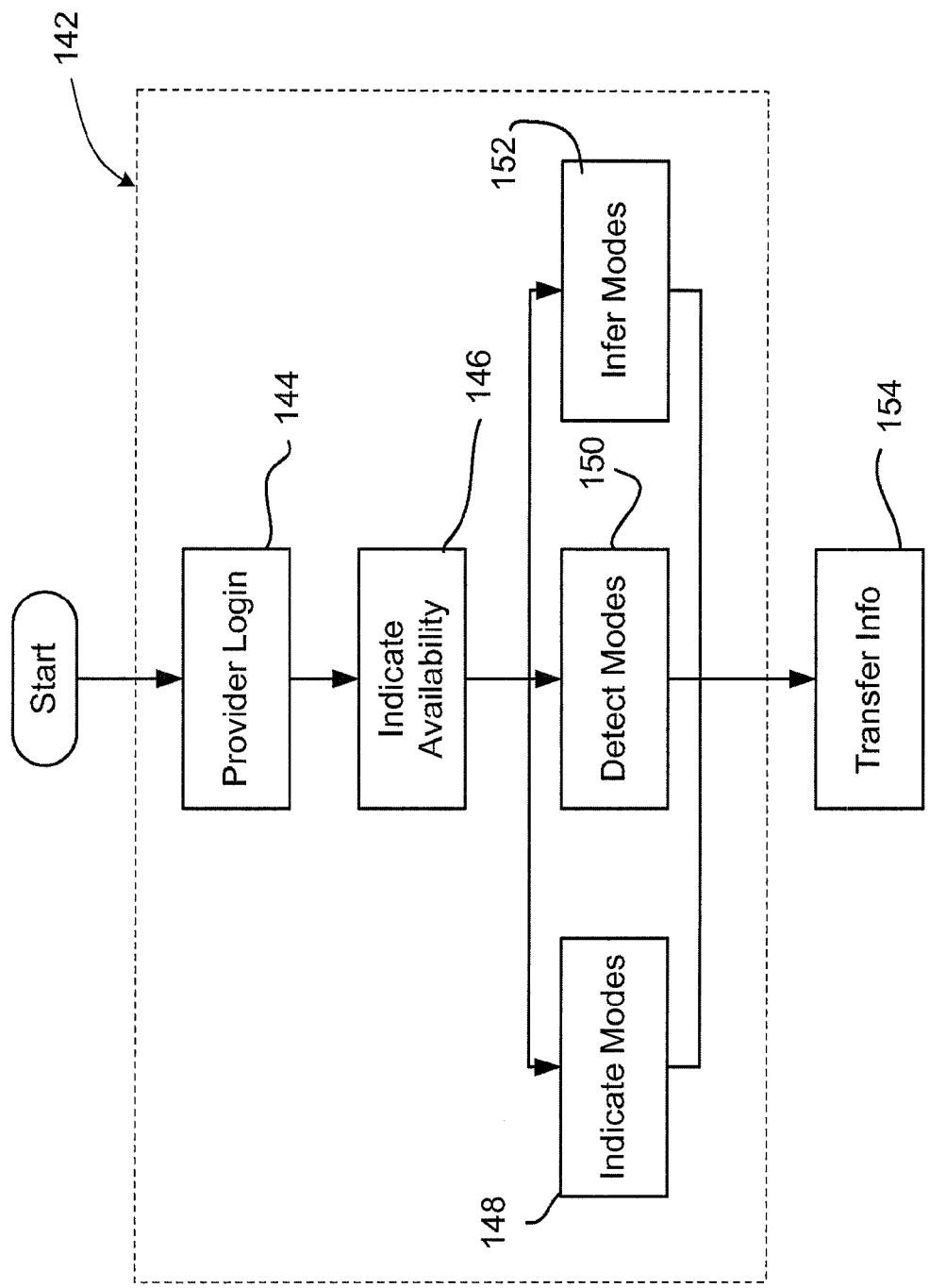
FIGS. 3, 4A-4D, 6 are flow charts of processes used in an engagement brokerage system.

Referring now to FIG. 3, the computerized system 110 tracks 142 the availability of providers 130 and consumers 120. When a provider 130 logs 144 into the system 100, the provider 130 indicates 146 (such as by setting a check box or selecting a menu entry or by responding to a voice prompt) to the tracking module 112 that he or she is available to interact with consumers 120. The provider 130 can also indicate 148 to the tracking module 112 (such as by setting a check box or selecting a menu entry or by responding to a voice prompt) the modes (e.g., telephone, chat, video conference) by which a consumer 120 can be connected to the provider 130. Alternatively, the tracking module 114 determines 150 the capabilities of the terminals 122 and 132 the consumer 120 and the provider 130 use to connect to the system (for example, by using a terminal-based program to analyze the hardware configuration of each terminal). Thus, if a provider 130 connects to the system 100 by a desktop computer and the provider has a video camera connected to that computer, the tracking module 112 determines 150 that the provider 130 can be engaged by text (e.g., chat or instant messenger), voice (e.g., VoIP) or video conference. Similarly, if a provider 130 connects to the system using a handheld device such as a PDA, the tracking module 112 determines 152 that the provider 130 can be engaged by text or voice. The tracking module 112 can also infer 152 a provider's availability and modes of engagement by the provider's previously provided profile information and the terminal device through which the provider connects to the system.

Providers participating in the brokerage network can have several states of availability over time. States in which the provider may be available may include on-line, in which the provider is logged-in and can accept new engagements in any mode, on-line (busy), in which the provider is logged-in but is currently occupied in a video or telephonic engagement, and scheduled, in which the provider is offline but is scheduled to be online at a designated time-point and can pre-schedule engagements for it. While not online, the provider can take messages as in offline state. Other states may include off-line, in which the provider is not logged in but can take message-based engagements (i.e., asynchronous engagements), out-of-office, in which the provider is not accepting engagements or messages, and standby, in which the provider is offline and can be paged to Online status by the brokerage network if traffic load demands it (in some examples, consumers see this state as offline).

The operating business model for the provider network employs a remuneration scheme for providers that helps assure that the consumers can find providers in designated professional domains (e.g., pediatrics) in the online mode. For example, selected providers can be remunerated for being in the standby mode to encourage their on-line availability in case of low discretionary availability by other—providers in their professional domain. Standby providers are also called into the on-line state when the fraction of on-line (busy) providers in their professional domain exceeds a certain threshold. In some examples, the transition of providers from standby to online and back to standby (in case of over capacity or idle capacity) is an automated function of the system.

The tracking module 112 transfers 154 information about the availability and the communication capability of the consumers 120 and the providers 130 to the scheduling module 116 using, for example, one or more well-known presence protocols, such as Instant Messaging and Presence Service (IMPS), Session Initiation Protocol (SIP) for Instant Messaging and Presence Leveraging Extensions (SIMPLE), and the Extensible Messaging and Presence Protocol (XMPP).

As noted, the system 100 includes access control facilities 114 that control how consumers 120 access the system and to what extent or level the services provided by the system are made available to consumers. The system 100 also stores and provides access to consumer information (e.g., contact information, credit and financial information, credit card information, health information, and other information related to the consumer and the services purchased or otherwise used by the consumer) and provider information (e.g., physician biographies, product and service information, health related content and information and any information the provider or the health plan wants to make available to members) and the access control facility 114 can prevent unauthorized access to this information. In some examples, the system 100 exports the consumer information for use in a provider's office or other facility.

The system 100 interacts with consumers and available data sources to position and direct their health matters to appropriate care providers. Consumers can use various tools of physician and provider profiling to exercise choice in selecting the providers they wish to interact with. The brokerage facilitates the communication between the consumer and his selected providers, allowing the consumer to follow-up as needed to establish a comfort level in his care. The brokerage supports transfer of these communications and any other results of the eVisit to non-virtual care points if such escalation is needed.

The brokerage can be considered as a first tier of medical care that is made available to consumers at home or at other locations. This first tier precedes typical entry points into a medical care setting, e.g., a physician's office or an emergency room. The brokerage enables consumers to explore concerns on, new or existing medical issues without the need to incur the time, cost, and emotional burden typically associated with the office visits or trips to the emergency room. To deliver such a comfort level, the system provides immediate access to tools that help define health issues, as well as, access to the appropriate automated and human mediated interventions. Consumers can discretionally engage (or escalate) the level of care they need to gain confidence in their management of such issues. The consumers' choices in this area span both the type of credentials of the provider they interact with (e.g., a nurse versus a board certified specialist), as well as the level of intensity (mode and frequency) of their communications (e.g., messages versus full video dialogue). The brokerage can export the information and workup gained during an encounter to a subsequent tier of services, such as a specific medical office or the ER (as well as care management services if offered by the consumer's health plan, hospitals and so forth). As such, the brokerage manages more costly medical service consumption (demand management) and serves as a pervasive tool for impacting basic medical care and follow-up and encourages appropriate health behaviors for the customer population at large.

There are various models for how consumers may gain access to the system. Consumers may purchase access to the system through a variety of models, including direct payment or as part of their insurance coverage. Health plans may provide access to their members as part of their service or as an optional added benefit. In some examples, health plans may receive information about their members' use of the brokerage to allow, for example, better allocation of resources and overall management of member's health care consumption. Employers may purchase access to the brokerage for their employees through whichever health plans the employer offers. Self-insured employers may purchase access for their employees directly with the brokerage. Providers may be compensated in several ways and may offer their services to the brokerage either independently or as part of a framework such as a provider network.

Similarly, there are numerous ways the brokerage can be packaged. As a health plan benefit, the brokerage expands a health plans ability to manage health care service consumption by their members. A health plan may provide access to the brokerage through an existing web portal through which members access benefit information and interact with their health plan. As an employee benefit, the brokerage supplements the employee's health coverage and may be presented, for example, through a human resources web site. In a direct-to-consumer situation, consumers may access the brokerage directly through its own web page. In some examples, the brokerage is implemented as an enterprise software system for a call center, such as one operated by a health care provider. Linked to other institutional users of the system (e.g., other participating providers), this can allow the provider to provide services to its patients that it cannot offer itself, such as 24-hour specialty consultations. The brokerage may also be used by a provider practice to allows its practitioners to provide care to the brokerage's members (and generate revenue) during off-hours or as a preliminary stage to office visits. This may also eliminate the need for an office visit with a primary care physician just to get a referral to a specialist.

The brokerage provides compensation for products and services provided. Access to the system 100 may be provided on a subscription basis, with consumers paying a fee (either directly or indirectly through another party, such as a healthcare plan or health insurance provider) to be provided with a particular level of access to the system. In exchange for providing products or services, the service provider may receive compensation from the consumer or from an organization that pays for the products or services on behalf of the consumer, such as a health plan or a health insurance company. In instances in which the consumer pays directly, the operator of the interface to the system that connected the consumer to the service provider may be compensated. In one embodiment, the consumer pays the operator, which keeps a portion (e.g., a percentage, a flat fee, or a co-pay) and pays the remainder to the service provider. In another embodiment, the consumer or the service provider pays a flat fee or percentage of the fee for the engagement to the operator. Where the service provider's compensation is paid by a health plan or insurance company, the operator may be paid a flat fee or a percentage of the fee for the engagement transaction by the health plan or insurance company. Alternatively, the consumer or the service provider or both may pay a fee (a co-pay or service fee) to the operator for providing the connection.

The Consumer Interface

Initiation of an Engagement

A consumer 120 engages with the brokerage system 100 to access a service provider 130. Several types of engagements may exist. Examples of these are described with respect to flowcharts in FIGS. 4A to 4D and user interface screens in FIGS. 5A to 5D.

Figure 4B:
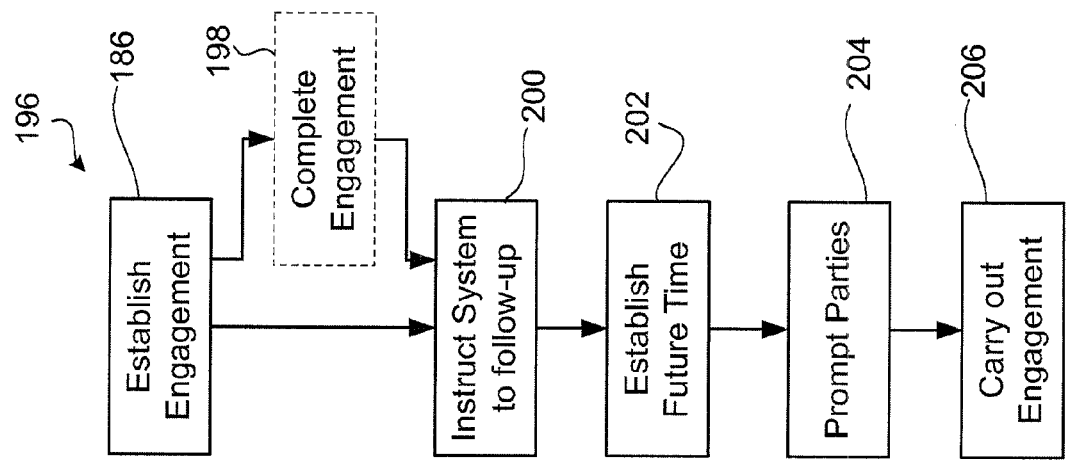
Figure 4A:
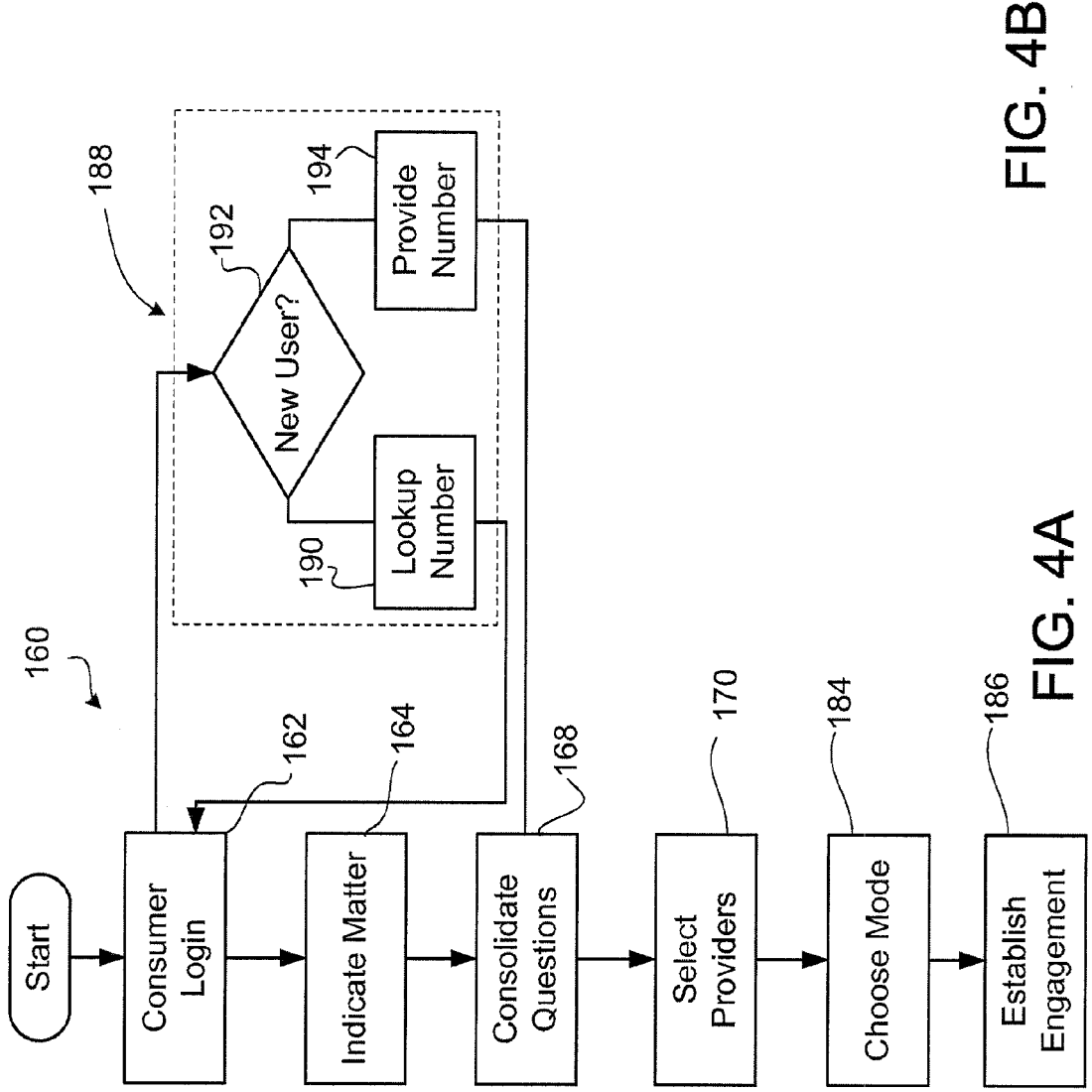
Figure 5A:
Figure 5B:
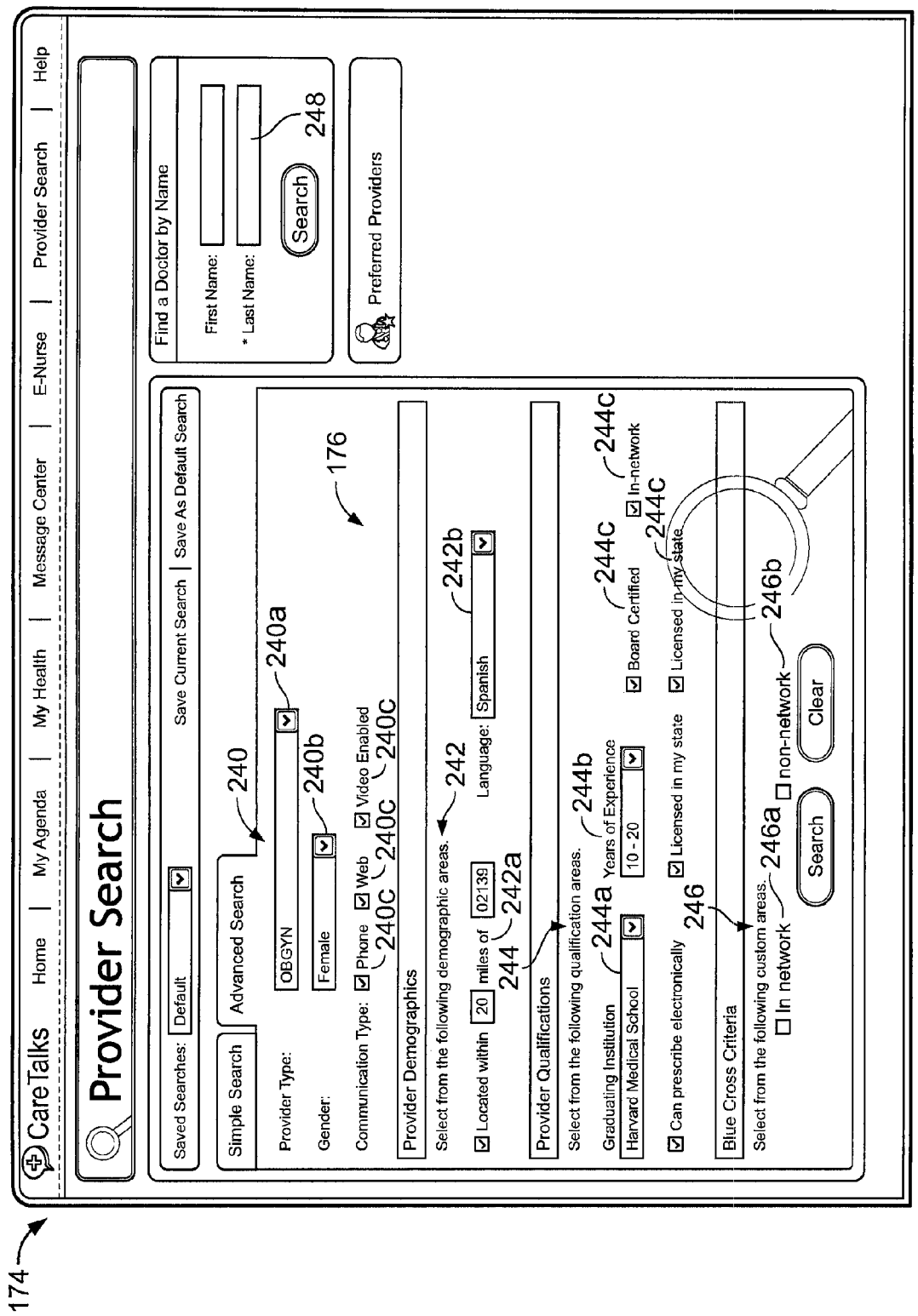

Referring now to FIG. 4A, a process 160 for establishing a consumer-initiated engagement is shown. In a consumer-initiated engagement, a consumer logs in 162 and communicates 164 a new matter he desires assistance or guidance on to the brokerage, for example, a health concern. For example, this is done on a web page 166, as shown in FIG. 5A. A component of the brokerage system 100, such as the consumer advisor discussed below, assists the consumer in consolidating 168 his questions and helps select 170 the appropriate providers to answer them. The web page 166 includes some initial questions 172, and another web page 174, in FIG. 5B, provides a user interface for entering additional criteria 176 to find a provider. A results page 178, in FIG. 5C, allows the consumer to select a specific provider 180 from a list 182 of providers identified based on the search criteria. Once a provider is selected and a mode of engagement is chosen 184 (see below), the scheduling module 116 establishes 186 the new engagement. In some examples, the brokerage associates 188 a unique identifier with participating consumers which can be used in subsequent interactions with the brokerage, such as associating records from multiple engagements. The consumer's health plan membership number or other similar, pre-existing identification can be used 190. If the consumer does not already have 192 a number, one is generated 194. The unique identifier can be used by the consumers to save their planned engagement for later retrieval.

Referring now to FIG. 4B, a process 196 for establishing a follow-up or prescheduled engagement is shown. Once an engagement is established 186 as in FIG. 4A or as one is completed 198, the two parties can instruct 200 a component of the system 100, such as the scheduling module 116, to pursue the established engagement or a follow-up engagement at pre-defined schedules or at future time points. The system uses 202 e-mail, automated telephone communication, or any other method of communication to establish a convenient time for both parties to accomplish the follow-up and then prompts 204 them to do so 206.

Figure 4C:
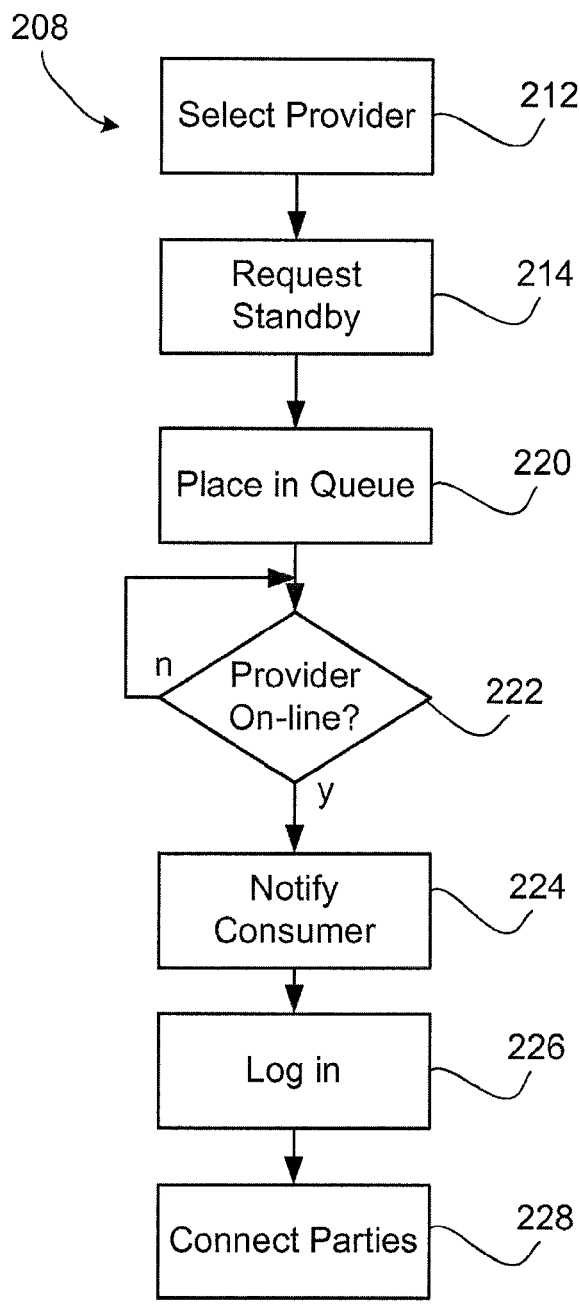
Figure 5C:
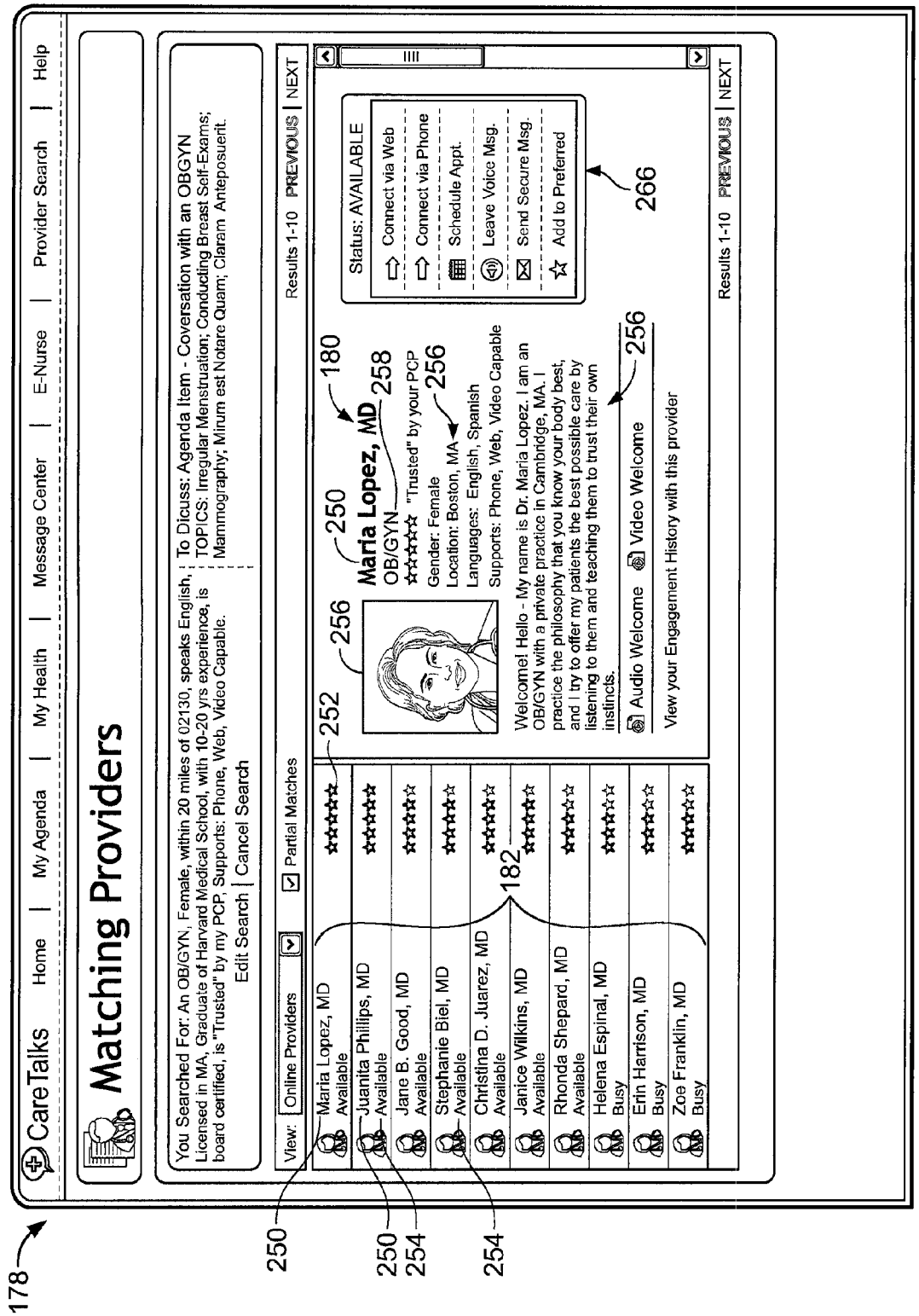
Figure 5D:

Referring now to FIG. 4C, a process 208 for a standby engagement is shown, with a user interface on a web page 210 in FIG. 5D. A standby engagement is similar to a consumer-initialized engagement. In a standby engagement, the consumer selects 212 a provider 180 or type of provider and requests 214 that a component of the system 100, such as the scheduling module 116, to notify the consumer by an appropriate communication, for example, e-mail, text message, or an automated phone call, when the selected provider is online and accepting engagements. In the example of FIG. 5D, the user has chosen to be called and input a phone number 216 and a limit 218 as to how long she will wait. The consumer request is placed 220 in a queue for the specific requested provider who is off-line (or for a type of provider for which all qualified providers are off-line). When the system determines 222 that the provider is available, the system notifies 224 the consumer. When notified, the consumer logs in 226 and is connected 228 to the provider.

As an option, a standby list for a provider may provide preferential queuing for some consumers. For example, preferential queuing may be provided based on prior engagements with the provider (e.g., preference is given to follow-up engagements) or based on a service tier (e.g., frequent user status) of that consumer. The brokerage can be configured such that it collects information about the consumer (e.g., answers to initial intake questions) and provides the collected information to the specific service provider prior to initiating any further engagements. For example, a consumer can store information during a consumer-initiated engagement as described above, park the information, and wait to be contacted when the specific selected provider is available.

Figure 4D:
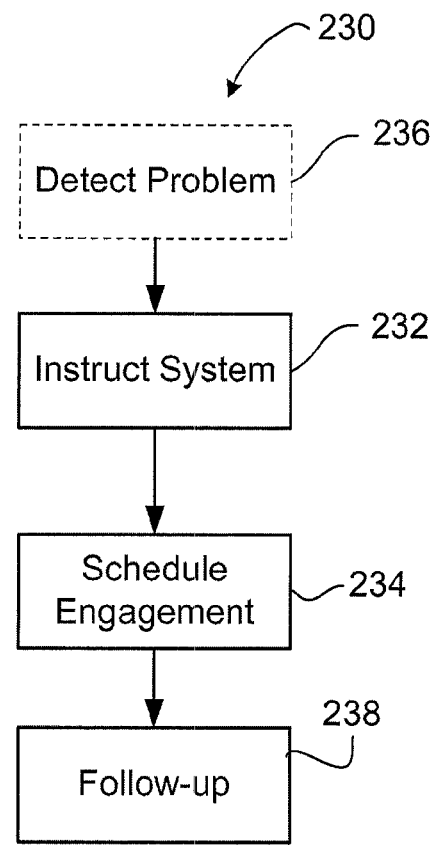

Referring now to FIG. 4D, a process 230 for an interventional engagement is shown. In addition to consumer-initiated engagements, a health plan (or another authorized entity) automatically instructs 232 the system to schedule 234 an engagement with one of its members. This scenario may be employed, for example, when a health plan member is consuming 236 costly charges or exhibits a high risk score. The system may also be authorized to automatically pursue 238 a low-intensity telephonic follow-up with members that would otherwise not be contacted for follow-up (e.g., Medicare or Medicaid patients).

Provider Selection

One capability of the brokerage is to extend a retail-like experience to the consumer. Consumers are able to spend time on the system to explore its participating providers whether they are currently available or are expected to be available at some other time. While the system can assist the consumer in identifying the most appropriate providers (see the consumer advisor function, below), it also allows the consumer to filter the provider list based on his preference and access a view of a provider availability matrix that changes as providers go on and off line.

An example of an interface by which consumers can select providers in a variety of ways is shown in FIG. 5B, mentioned above. In the health-care based example of the illustrated page 174, various criteria 176 can be used to filter the available physicians. Basic details 240 indicate the consumer's preference for the type 240a and gender 240b of the provider and what modes of communication 240c the consumer wants to be able to use. The user can also specify demographics 242 including location 242a and languages spoken 242b. Qualifications 244 may include education 244a, years of experience 244b, and various other criteria 244c. The consumer's health plan may offer additional searching criteria 246, such as whether a provider "must be in-network" 246a or whether the consumer can consult with an out-of-network provider 246b. A consumer can also use a search box 248 to search for a provider by name.

Consumers may select providers according to attributes of the provider, such as a geographical area where the provider is located or which professional organizations have accredited the provider (e.g., whether a doctor has board certification in cardiology). Any metrics within the provider profile (discussed below) can be used to define a list of providers that meet the consumer's preferences.

Once the consumer enters her search criteria 176, the results are shown on the web page 178 in FIG. 5C. As mentioned, a list 182 of providers is presented. This list may indicate each providers name 250 and rating 252 and whether the provider is available 254. For the selected provider 180, additional details are shown, including her picture 256, specialty 258, demographic information 260, what types 262 of connections she can use for an engagement, and personal information 264. Tools 266 allow the consumer to initiate or schedule an engagement.

Providers already associated with the consumer may appear on the consumers' short list. Association may be based on historical engagements and may extend to the health plan's feed of claims (i.e., all providers that submitted claims for the consumer). When reviewing the list of historical engagements, consumers are able to access the engagement audit and the ranking they have attributed to any engagements in the past.

In certain modes of deployment, there are functional attributes that may impact the consumer's selection. In most health-plan distribution modes, consumers may opt (or be limited) to see only providers that are "in-network" according to their insurance coverage product. Selecting an "out-of-network" provider may incur higher out-of-pocket costs. Another example relates to a deployment of the system in disease management and health coaching settings (e.g., a call center). In this case, the plan may require that the consumer can select only nurses that are associated with the disease management program with which the consumer is associated.

Regulations introduced by the federal government in August, 2006, require all federal bodies offering medical coverage (including Medicare, Medicaid, and military, and federal employee plans) to publish their ratings of health service providers (physicians and hospitals) to the general public. The system can allow the consumer to search such sites automatically for a selected provider prior to an engagement. Other sources of reference data may include state publications on morbidity, mortality, and legal actions against providers, or databases maintained by third parties.

Once a consumer has defined a collection of criteria to filter and find a provider, the system can offer tools to shorten the process in the future. Consumers may be able to save criteria-sets as named searches and benefit from notifications when a search list surpasses a certain level of availability that may encourage the consumer to log in and communicate with a provider.

Modes of Engagement

The brokerage allows consumers to engage provider's e.g., health professionals "on demand" based on provider availability. Engagements can be established in various ways, including:

1. Passive browsing—Reference health content is accessed on the brokerage's website. The website can support the use of licensed content packages from other vendors to meet the variable preferences of health plans. For example, key content vendors include Healthwise™, ADAM™, Mayo Clinic™ and HealthDay™. Content libraries provided by such vendors offer a combination of articles, imagery, interactive tutorials and related tools that allow consumers to access content relevant for their health issues. Many health plans and major employers already possess a license for the use of one of these content packages.
2. Health Risk Assessments—The system acquires information from consumers through automated interaction (e.g., rules-based interaction) in order to crystallize their needs (e.g., medical risks) and better direct them. Assessments span from general health to very specific medical conditions and follow a path of questioning that dynamically tailors itself based on information already retrieved (e.g., using predefined rules). As assessments progress, the system constructs engagement suggestions that the consumer can exercise. Each suggestion represents both the question to the provider and the type of provider appropriate to answer it. Consumers may choose to simply launch such engagements or apply their own discretion as to the phrasing and the selection of the recipient provider. This is discussed in more detail below in the context of the consumer advisor.
3. Asynchronous correspondence—The lowest level of true provider interaction is by way of secure messaging. The question or topic of the engagement is sent to a selected provider (whether online or not) and can be answered by this provider at her leisure. Turnaround times are monitored by the system and are part of the credentials of the provider used for her selection by consumers. The system informs the consumer once a response has been received and can allow the consumer to redirect the question if he needs more urgent response time. For example, typical types of asynchronous correspondence include e-mail, instant messaging, text-messaging, voice mail messaging, VoIP messaging (i.e., leaving a message using VoIP), and paper letters (e.g., via the U.S. Postal Service).
4. Synchronous correspondence—Several forms of synchronous correspondence allow the consumer and the provider to engage in real-time discussions.
5. Synchronous text correspondence—This may be referred to as a "Chat" module where both sides of the engagement type their entries in response to each others' entries. The form of communication may be entirely text based but is still a live communication. Examples include instant messaging and SMS messaging.
6. Web-based teleconferencing—The use of broadband network connections allows for real-time voice transmission over the Internet in what is referred to as full duplex (i.e., both voice channels are open at the same time). Consumers can opt to have a voice conversation with their providers using, for example, their computer's speakers and microphone. Web-based teleconferencing may use VoIP, SIP, and other standard or proprietary technologies.
7. Telephonic conferencing—Consumers who wish for a direct telephonic communication with a provider or who are not comfortable using their computer may use a traditional telephone for interaction with a provider. The consumer may use a dial-in number and an access code that connects him to the brokerage's servers. Providers are linked to the servers via VoIP, other data-network-based voice systems, or their own telephones. Telephonic conferencing may also allow consumers to request "call me now" functions, in which the provider calls the consumer (directly or through the brokerage).
8. Video conferencing—The system can support video conferencing to allow consumers to exhibit physical findings to providers if such disclosure is needed. Consumers and providers may also simply prefer face-to-face communication, even if remote. Small digital cameras, referred to as webcams, attached to or built in to personal computers or laptops can be used for this purpose. Video conferencing can be provided by standard software or by custom software provided by the brokerage. Alternatively, dedicated video conferencing communication equipment or telephones with built-in video capabilities can be used.

9. Semi synchronous correspondence—Some engagements of a consumer with an online provider include both synchronous and asynchronous interactions. Part of the engagement takes place by immediate messaging between the two, but the provider may ask the consumer to take occasional asynchronous assessments if, for example, a generic line of question is desired. This allows the provider to operate more than one consumer engagement at a time while each consumer is constantly engaged. For example, semi-synchronous correspondence includes a combination of e-mail, instant messaging, test messaging, voice calls and mail messaging, and VoIP calls and VoIP messaging.

Interactive Voice Response Engagements

Interactive Voice Response (IVR) systems allow for the deployment of interactive audio menus over the phone. The caller can navigate between options, listen to data-driven information, provide meaningful input, and engage system functions. IVR engagements extend the reach of the system to the telephone as a portable consumer interface to launch an engagement in addition to the Web-based interface. Consumers select a pin code on the application to authenticate their identity if they call in. Several types of engagements can be carried out through an IVR system using logic like that shown in FIG. 2B. For dial-in engagements, the consumer calls in and invokes a telephonic engagement with an available provider. The IVR system extends the consumer's ability to select a provider to the phone so that the consumer's interaction resembles one carried out on the Web.

The IVR system can also be used proactively to pursue consumers who need a follow-up. At the time of a follow-up, the system recalls the provider with whom the follow-up is desired (or the type of provider in case the follow-up is not restricted to a specific provider), identifies that the provider is available for an engagement, and attempts to contact the consumer over the phone to establish a connection for the engagement. Once contacted, the consumer can decline or ask postpone the call. If the consumer takes the call, the connection is made. When consumers are pursuing an engagement with a provider that is either busy or currently offline (e.g., a specific provider or a type of provider with few participants), the IVR system allows the consumer to park in a standby mode until the provider is available. When the provider is available, the system calls the consumer, identifies the provider to the consumer, and verifies that the consumer is still interested in pursuing the call with the provider. If the consumer is still interested, an engagement is connected.

In addition to launching engagements, the IVR interface allows consumers to interact with other services offered by the brokerage. For example, consumers can instruct the system to fax a transcript of their information to a fax machine that the consumer identifies by keying in or speaking its phone number. Using such a function, a consumer makes key information available to, e.g., emergency room personnel or to a provider in an office visit, without the need to plan, collect, print, and carry the information to that encounter.

IVR hardware is readily available from telecommunication vendors and can be programmed to operate in the context of the brokerage framework. Authentication is provided through a PIN number or by other standard methods.

Engagement Auditing

In some examples, material elements of an engagement are audited by the brokerage to establish a work-up record of the consumer. Such a record of consumer entries, recordings, and provider notes, together with time stamps and identification of registrars, is available to the consumer at any time for future reference. A consumer may choose to share this record with other providers within the brokerage or to export it to an external point-of-care such as a provider office, an emergency room, a care manager, or an external record management system such as a regional health information organization (RHIO) (and to similar entities in non-medical implementations). Auditing may also include various degrees of automated entry of standardized coding to allow effective rule-based moderation of the system based on clinical (for example) insights captured during the engagement. In some examples, the manners of auditing and coding are compliant with the Health Insurance Portability and Accountability Act (HIPAA).

Engagement Recording and Transcription

The system 110 allows an engagement conducted using a voice technology, such as telephone, VoIP, or a video call over the web, to be recorded. As the system generates an audio file, it offers consumers services associated with the file. Based on a consumer request or setting to produce a transcript, the system forwards the file to a third party vendor to perform transcription of the file and return a textual representation of the engagement. Such text is incorporated into the consumer's record, communicated to an external party, or used as the basis for future engagements. In some examples, the transcription may be performed by voice recognition software. Transcription services can be bundled with encoding and translation services. The consumer may also request that the audio recording be made available over the phone or as a data file to a third party (e.g., the consumer's personal provider). In some examples, consumers are able to replay the recording from either the web client or a telephone as part of the IVR system.

Engagement Redirection

In some examples, a consumer redirects an active engagement to another provider or provider type. A consumer may also redirect an engagement to employ a different mode of communication with the current provider (e.g., move from a text chat to a phone conversation). The audit of the information and work up established before the redirection becomes the basis for the new engagement. In some examples, a consumer redirects an engagement that concluded in the past as a way to continue follow-up on the same issue.

Consumer Advisor

Another utility in the brokerage, the consumer advisor, assists consumers in determining what actions to take, for example, which types of providers to consult. The consumer advisor acts as a facilitator of engagements between consumers and providers, similarly to the way a nurse might interact with a patient in a health care system. In some examples, the consumer advisor is operated using a rule-driven engine embedded in the system 110 that draws from both consumer intake data and programmed clinical knowledge. The consumer advisor helps the consumer identify issues that the consumer should discuss with a provider in the system, collects data to contextualize and shorten the time needed for the discussion, and helps orchestrate engagements with the appropriate type of providers, presenting the collected intake information to the providers prior to the commencement of the engagement itself.

The consumer advisor walks the consumer through the process of using the brokerage and helps the consumer acquire the appropriate services, minimizing the time spent and cost to the consumer in determining which services to use. In some examples, the consumer advisor packages or formats the information it has collected to export it to a non-virtual provider (e.g., a consumer's primary care physician) for further follow-up, even if the consumer did not end up in an engagement. The consumer advisor operates as an assistant to the provider during an engagement, working directly with the consumer.

Figure 6:
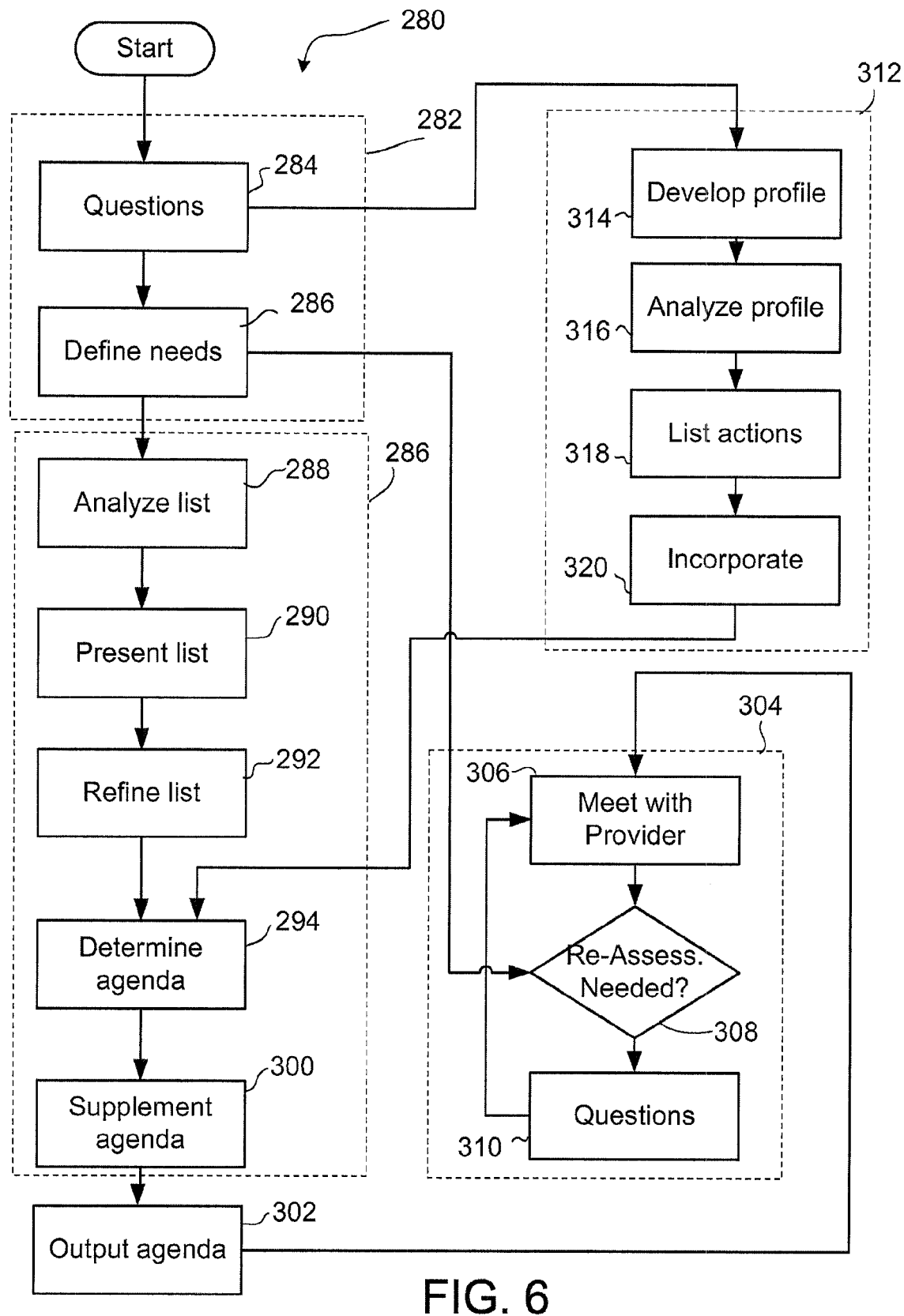

FIG. 6 shows an example process 280 used to implement the consumer advisor. An intake stage 282 asks 284 the consumer a series of questions that either pin-point the area of concern or capture relevant information about the needs (for example, the health) of the consumer in that area. In some examples, this process is equivalent to what the healthcare industry calls a Health Risk Assessment (HRA). The intake stage 282 identifies or defines 286 one or more of a consumer's needs or problems. The result of the intake stage 282 include a list or a narrative summary of the issues that should be presented to the provider. The intake stage enables the consumer to exclude topics he prefers not to discuss or to add topics manually. The result of the process is what physicians or lawyers call intake, a desired step in a first-time office visit or client engagement. This relieves providers from performing the typical extensive intake process during an engagement. Because the information the provider would collect has already been gathered by the intake stage 282. In the health care example, the intake stage 282 covers topics that extend to both medical conditions and issues (e.g., pain in left shoulder, not associated with exercise) as well as general health and wellness assessment profiling (e.g., the patient is a female over 40 and had not had a mammogram, the patient is overweight, the patient is having trouble sleeping).

The information obtained from the intake stage 282 is analyzed 288 in an analysis stage 286 to determine a list of topics concerning health issues. The consumer advisor presents 290 the list of topics about the consumer's needs to the consumer and allows the consumer to further refine 292 the list by adding or removing topics. In the health care example, generating the list includes codifying the conditions, issues and general state of health and wellness of the patient to allow internal profiling of the patient and to facilitate future engagements. Once a list of topics is defined, the analysis stage 286 determines 294 an engagement action plan or agenda for the consumer, suggesting the type of providers most appropriate to discuss each topic and the relative priorities of such discussions. A web page 296 presenting an example agenda 298 is shown in FIG. 7. The consumer advisor may supplement 300 the agenda with links to consumer content information to educate the consumer about the condition or issue prior to his engagement with the provider. The action plan is output 302 in several ways. In some cases, a consumer prints (or downloads and saves) the action plan and takes it to his live provider. In some cases, the action plan is transmitted to the consumer's live or primary provider automatically.

The action plan is also output 302 to the scheduler module 116, which locates providers and establishes engagements, as discussed above with regard to FIG. 4A, for the most appropriate provider(s) available for each of the action plan's item(s). The consumer uses the system 100 to engage such provider(s) or to find other available providers, and to sequentially engage providers appropriate for each of the topics on the consumer's engagement action plan. The consumer can also re-prioritize the items in the action plan and save the action plan to use at some point in the future. A consumer may use the list as basis for entering into multiple engagements (with multiple providers) or allow the first provider engaged (or the consumer's personal provider, such as a primary care physician) to review and orchestrate the management of all issues in the list. The scheduler module 116 allows the consumer to use the system 100 to engage available providers in any suitable mode (for example, by chat, by video conference, or by voice communication) or to enter the standby list for providers currently not online.

In certain engagements, the provider enhances interaction with the consumer by using a re-assessment process 304 to acquire further information about the consumer's condition. During an engagement 306, the provider invokes 308 the re-assessment process 304 to cause the consumer advisor to interact 310 with the consumer on one or more specific intake assessments or assessment forms. For example, where the initial intake did not determine the possibility of a specific issue or condition, a treating physician, after consultation with the consumer, can ask for a specific intake process to be given or taken again (for example, where the consumer omitted an important symptom). Once the re-assessment is completed, the treating physician or a new physician (in the health care example) can have 306 a new live engagement with the consumer.

This assessment process 304 may be repeated, with the consumer undergoing further assessment or repeating assessments to collect further information for the provider. In some examples, the intake stage 282 determines, based on information provided by a previous provider, for example, that the consumer needs a re-assessment and the nature of the re-assessment, such that when the consumer returns to the intake stage 282, the consumer is prompted as to whether the consumer wants to proceed with the re-assessment or perform intake for a new engagement or different condition or disease.

In some examples, the consumer advisor includes a health improvement function to assess a consumer patient's current overall health and wellness state, a specific area of the health and wellness state, or treatment for a specific condition, issue or symptom. A profiling operation 312 is performed using the data collected by the intake stage 282 to form a profile of the patient. This data include the consumer's goals, where the consumer wants the consumer's health state to be in the future, and desired changes in the consumer's overall health and wellness state or in a specific area of the consumer's health and wellness state (e.g., body weight, BMI, cholesterol level, etc.), or treatment for a specific condition, issue or symptom. After developing 314 the profile and analyzing 316 it, the consumer advisor lists 318 the actions that the consumer should take to achieve these goals and incorporates 320 the actions into the consumer's action plan. In addition to recommending treatment, the health improvement function also promotes actions in the area of education, including static content and active engagements.

The health improvement function also determines a regimen for the consumer to follow to achieve the goals. Where necessary, the consumer can be directed to the scheduler module 116 to connect the consumer with a provider to assist in developing the regimen. For example, the consumer can meet with dietician to assist in the development of a dietary regimen or a personal trainer for the development of an exercise regimen. The consumer can periodically interact with the health improvement function to track her progress toward her goal. The information about the consumer's progress and updates as to the consumer's profile information are collected using the intake stage 282.

The steps of the process 280 may be implemented in a single module or in several functional components or modules including an intake module and an advisor module. The consumer advisor may be implemented as a module within the server 110, similarly to the tracking module 112 or the scheduling module 116, or it may be a self-contained module. The scheduling may be carried out by the scheduling module 116 through an interface to the modules carrying out the advisor process. To provide continuity to consumers, the interface may be implemented as part of the interface shown in FIGS. 5A-D.

The consumer information collected by the intake process may be stored in the databases 118 as part of the overall brokerage. In some examples, the consumer information is protected and secured from unauthorized access and in compliance with the various legal requirements for storing private consumer information (for example, HIPPA governs access to an individual's health care information). The database 118 may also the process logic and rules data including the business logic of an application or rules for a rules engine that implements the consumer advisor module.

The system 110 keeps track of where the consumer 120 is in any of the processes so that the consumer 120 can log out and, upon his return, be taken to the same point where he left. After the consumer 120 has completed a section of his action plan, for example, after a patient has been successfully treated for a condition, the system 110 archives the related data and stores it as part of a virtual consumer record system in the databases 118. In some examples, a virtual patient record system is used as a source of data for various health assessment and health risk studies. Patient data can be accessed anonymously, for example, so that researchers can study patient data without obtaining the identify of any of the patients.

Auxiliary Services

Other services can be incorporated into the overall brokerage. Such auxiliary services extend the completeness of the service's offering or allow for advanced functions that can improve the end-user experience in a substantial way. The brokerage architecture allows incorporation of such auxiliary services either as part of the brokerage framework or as plug-ins using $3^{rd}$ party vendor components. Such auxiliary services may be positioned inside the brokerage console to facilitate a consolidated user experience independently of who ultimately provides them.

A consumer data repository includes collection of parametric and non-parametric data. In addition, the repository holds consumer information, such as health and wellness information. For prescription filling, a provider prescribes medications to a patient over the web and submits the prescription to a local pharmacy for pick up. Such services may include components of prescription clearinghouses like SureScript™ or RxHub™. Where appropriate, the system is designed to interface with such services. There are, of course, legal constraints on such offerings.

In targeted self-help programs, a provider may advise a consumer to engage in a certain action plan that uses only intermittent provider involvement and is primarily focused on ongoing interaction by the consumer with computerized modules. The brokerage may offer information regarding a consumer's current eligibility for services or benefits as well as general information on offerings, programs, and enrollment in special products offered by, for example, a health plan that is providing the brokerage to its members. This information may also come from employer-operated benefit services. If consumers are enrolled in health-related financial products like health spending accounts, various updates on current standing are be presented through the console. This information is updated, linked to, or summarized by the plan, the employer, or an affiliated financial institution managing the consumer's account. Similarly, retirement plans or brokerage accounts might be linked, for example, if the brokerage is provided by the consumer's employer or bank to provide financial planning advice. Consumers may be given access to relevant and targeted clinical content from packages that are included in a specific service subscribed to by or on behalf of the consumer. These may include packages related to clinical, health, wellness (e.g. diet and exercise), preventive medicine, medication, coaching, mental health, and other disciplines.

Information Portability

The brokerage extends the result of any engagement to a physical point of care or service provider to allow continuation or escalation of services beyond those provided in the electronic encounter. For example, a textual transcript of an engagement is forwarded to a desired provider. If the provider is a participant in the brokerage, the provider accesses the transcript directly. If the provider is not a participant, other modes of access to the transcripts may be used, such as e-mail or fax or temporary access may be given to the non-subscribing provider. In some examples, the service may compensate a provider for reviewing a summary of his client's on-line engagement with another provider. This keeps the primary provider informed, leading to better service for the consumer, and making the eVisit system more palatable to the primary provider.

The brokerage may also supplement the record of the engagement with additional information, such as pointing out to a physician what treatment options the patient's health plan would prioritize for an illness noted in the record, or what preventative treatments the patient may be due for.

A consumer may opt to receive or forward his entire record on the brokerage's system for either safekeeping or as part of a record transfer to another service, for example, if the consumer changes health plans. In some examples, the brokerage allows consumers to request such a transcript to be transmitted in electronic form or to be loaded onto a selected medium. Outbound communications can be explicitly approved by the consumer, for example, to conform to HIPAA requirements for managing protected health information (PHI) or other consumer privacy policies or regulations.

Assuring Treatment Continuity

Consumers are more likely to use the brokerage if they perceive it as a valid tier in their relationships with their service providers, which is more likely if there is continuity between engagements, whether live or on-line. The workup performed on the brokerage facilitates the consumer's non-virtual relationship (rather than being redundant or contradictory) and thus encourages participation by both consumers and providers. The brokerage provides several features to achieve this goal. In some examples, the brokerage engages concierge practices in key geographic locations to provide non-virtual care to consumers who are otherwise managed only through brokerage-based engagements.

A service guarantee is provided to the consumer that any workup performed on the system is made available to his local service provider (e.g., his primary care physician) or requested point of care within a set number of business days electronically and another number of business days by paper statement. The consumer can also receive, for his own safekeeping, an assurance in the form of transcripts of each transaction.

For providers who do not participate in the brokerage, a referral guarantee is provided to the consumer's local service provider (e.g., his primary care physician) that her role in coordinating the care to the consumer will not be harmed. As such, the system acknowledges the local service provider's role visually to both the consumer (e.g., while in engagement with another provider) and to any participating providers with whom the consumer interacts. The designation of a certain local service provider as, for example, the PCP of the consumer, automatically triggers a behavior in the system that continues to update that local provider on the activity around "her" consumer. Another function that can further cement the role of the local service provider is an automated referral in which the participating provider can refer the consumer to an office visit only with that local service provider if additional workup is needed. This allows the local service provider to increase her visibility and receive more traffic merely by cooperating in her customers' use of the brokerage.

In some examples, a quid-pro-quo feature extends the treatment continuity offered to the consumer beyond forwarding engagement information to a non-virtual service provider. It allows consumers to continue a virtual engagement (or follow up on one) with a participating provider operating a real-world practice. Because participating providers have access to the brokerage's online interface, transitions between on-line and live providers are more informed. The consumer benefits from being able to pick up where he left off in the on-line engagement and assure continued documentation of his non-virtual visit in his service-based records.

Consumer Incentives

In some examples, health plans or other entities offering the brokerage to their customers incorporate automated incentives. Such incentives reward consumers for activities that yield favorable health outcomes (in the example of a health-plan-provided service). Incentives are provided to encourage consumers to, for example, become educated about the nature of a chronic condition with which the consumer has been diagnosed, engage in a conversation that yields advanced detection of a major health issue, perform online follow-up on conditions that warrant it (e.g., coronary artery disease or Diabetes), and participate in engagements that yield higher drug regimen compliance in select medical conditions. The system allows such incentives to be distributed automatically and promoted to appropriate consumers to encourage, for example, desired health behavior and medical management.

Interface with External Data Sources

To facilitate engagements between the consumer and the provider, the system acquires information from available systems automatically and uses the information to prepare providers at the beginning of an engagement. Such interfaces include both synchronous (e.g., web services) and batch updates from, in the example of health care, eligibility data, claims data, Pharmacy Benefit Management (PBM) information, predictive modeling, provider feeds relevant for consumer referrals, other standard-coding feeds using, e.g., ICD, CPT, HCPCS, NDC, SNOMED, or LOINC, formulary information relevant for Rx drug choice determination and preference, Customer Relations Management systems (CRM), and external messaging systems and queues (e.g., My Yahoo!, personalized RSS feeds).

Management and Analysis of Raw Data Inputs

In some examples, the brokerage accepts raw data inputs such as claims, pharmacy data, and lab data, from a variety of sources typically used by large clients (e.g., health plans, care management companies). The system validates the correlation between incidental entries in the raw data and the profile of the consumer. To do this, the system applies customizable analytic rules that tag a consumer as diabetic, for example, based on lab results, rather than flagging a consumer as a diabetic merely because he had a test to exclude diabetes (e.g., where the ICD code for the text doesn't indicate its outcome).

Service Providers

Provider Enrollment

Figure 8:
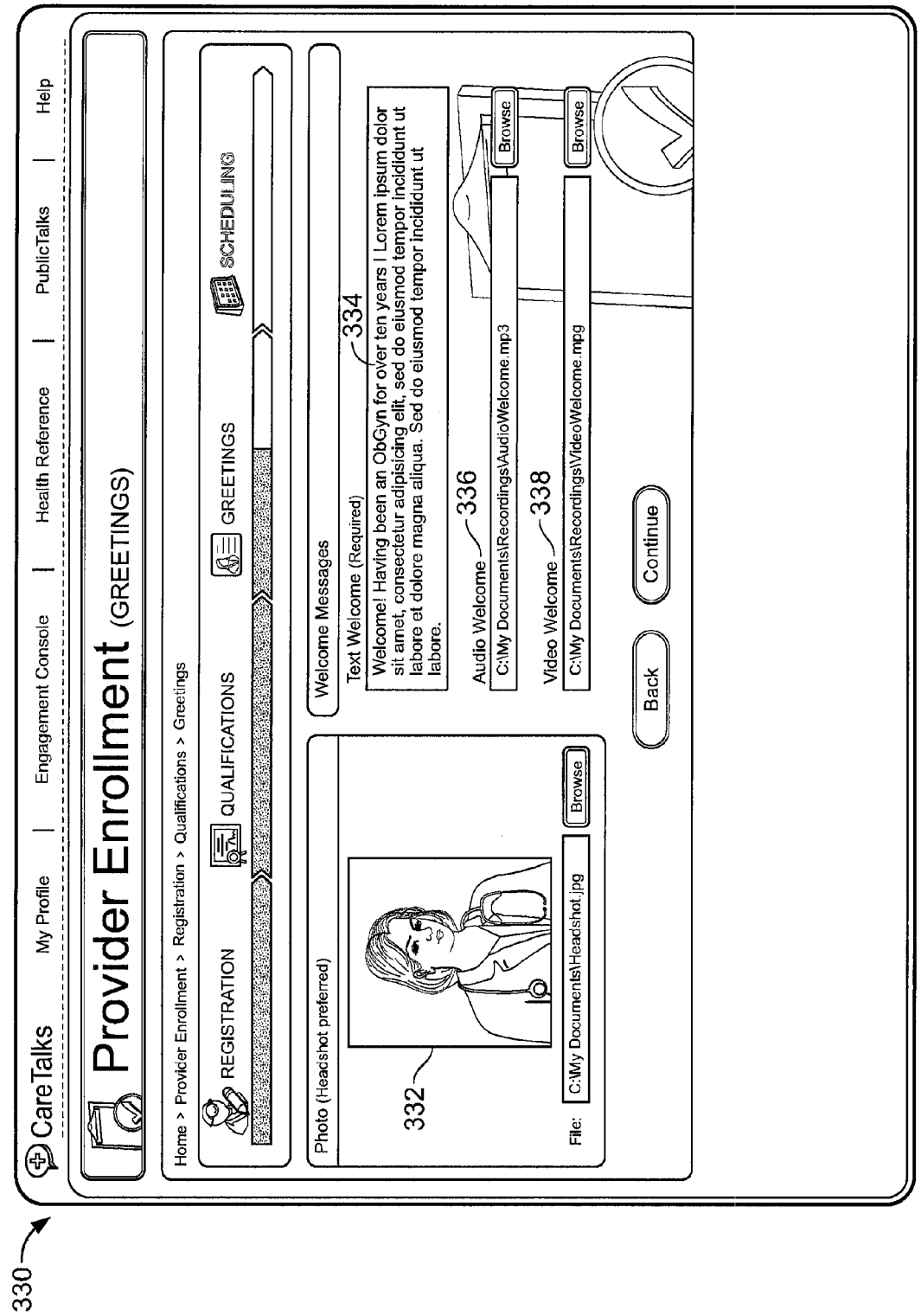

Service providers are the individuals responding to consumers queries and participating in engagements. For example, in a health care setting, service providers include doctors, nurses, and other medical professionals. Such providers participate in the brokerage while maintaining their affiliations they may have with any sort of professional engagement in the non-virtual world (e.g., a hospital appointment, a clinic or a private practice, partnership in a law firm). Providers on the brokerage network are verified to hold their claimed credentials prior to being permitted to accept engagements with consumers. Once verified, providers agree to the terms of the brokerage, such as payment for their time in performing engagements, the protocol of conduct desired, and the ramification and distribution of liability in case of violations of that protocol. These are similar to the agreements providers would make when joining a group practice or a hospital in the non-virtual world. An example web page 330 for one stage in the enrollment process is shown in FIG. 8.

Prior to joining the brokerage network, a provider establishes a profile that allows consumers to select him as the target service provider of an engagement. Providers are profiled using verifiable information from provider registries (e.g., the American Medical Association (AMA) for physicians or the American Bar Association (ABA) for lawyers) as well as by a self-statement. The profile is used for several purposes, including determining the relative cost of the provider's time to either the consumer or the brokerage sponsor (e.g. a health plan that is paying for the service), and providing consumers with information that may be relevant to their choice to engage one provider versus another. Some information about the provider is verified by the brokerage (e.g., Tax ID, education, professional certification, demographics, and contact information), and some is acquired during the provider's participation on the brokerage. Such data may include length of service, number of engagements, consumer satisfaction, projected availability, etc. A provider may also provide a general introductory note, a picture, and voice and video welcome snippets. Providers may also add other information they deem relevant for consumers (e.g., a list of publications and honorary appointments) A table 340 in FIG. 9 lists example profiling criteria that can be populated during enrollment in a medical context. The table 340 includes example criteria 342, specific examples 344 of each criterion 342, and an indication 346 of whether that criterion would have an impact on engagement cost.

Providers participating in the brokerage may come from one or more networks of service providers. Individual service providers are also able to register and enroll with the system. Individual service providers may be independent service providers not affiliated with a provider network, or service providers affiliated with a provider network that is not itself affiliated with the brokerage. This allows service providers (or other service provider networks) outside of a selected service provider network to participate in the system.

Provider Introduction

As part of the provider selection process described above, consumers benefit from access to introductory material from the provider. As consumers search for providers to meet their needs, they can select to view only providers where such material is available, producing an incentive for providers to take advantage of such capability. The example page 330 in FIG. 8 allows a provider to upload such information. Introductory material may include the provider's picture 332, a text welcome 334, a welcome recording 336, a video introduction 338, or a link (not shown) to the provider's home page in a clinic or hospital. The introductory material may also include an Internet link (not shown) provided by the brokerage that shows the provider's credentialing on a recognized public site (e.g. The American Medical Association).

Provider Certification

In some examples, the system certifies service providers (or networks of service providers) to enroll and participate in the system. This may use certification standards established by outside agencies, such as the AMA or ABA. A provider wishing to become enrolled in the system registers with the system and provides his credentials, such as board certifications, years in practice, employment history, residencies, and education. The system confirms this information and evaluates the provider as a potential provider in the system. In addition, the system may also contact existing providers in the system, such as those with the same specialty or board certification or who have worked with or attended school with the candidate provider, and ask them to provide a peer review rating of the candidate provider. In some examples, the certification process is provided by a third party organization or by the same organization that provides the system for connecting service providers and consumers.

In some examples, the certification process considers load balancing of available or participating service providers in order to encourage service providers of specialties that have low average availability or are in high demand with respect to the consumer marketplace to enroll and participate in the brokerage. The brokerage may also limit the enrollment of service providers in specialties that have high average availability or are in relatively low demand to service providers with credentials that meet or exceed the credentials of service providers already participating in the system. The system maintains information about the specific needs of the consumers and the availability of service providers specializing in areas that can meet the needs of the consumers. Using this information, the system identifies which areas of specialization would benefit from additional service providers and which areas are underutilized and possibly in need of reducing the number of service providers or adding additional consumers. Because the system can connect service providers and consumers who are separated by great distances and who may not normally interact in person, the system allows service providers who are underutilized in their current location to make up for a shortage in another location.

Provider Ratings

To further improve the ability of consumers to choose appropriate service providers, the brokerage includes a utility for rating the products and services provided by the service providers or by a service provider network. The consumers provide feedback (positive and negative) to the system about the products and services provided by a particular service provider. For example, in a healthcare system, the patients can provide an evaluation of the quality of treatment or bedside manner provided by a physician. In addition, the service providers provide feedback and evaluations of the products and services provided by other service providers. For example, a primary care physician can provide an evaluation of the products and services provided by a specialist to which he referred one of his patients.

In some examples, this information is used to reconsider the certification of service providers participating in the system. Periodically, the system perform a re-evaluation process on each of the service providers participating in the system and eliminates or locks out service providers that do not meet certain criteria or a minimum level of performance with respect to consumer and peer evaluations. Newer service providers are enrolled to participate in the system for a probationary period where they are allowed to continue only if the evaluations of their products and services are satisfactory or are above a predefined threshold for performance.

As part of the provider profile (and as a way for consumers to limit their search), the system continuously updates each provider's profile with metrics reflecting the quality of his or her interaction with consumers. The metrics are updated at the conclusion of every engagement to allow providers immediate feedback as to their level of service. In some examples, all searches for providers on the system are sorted by provider rating by default, promoting higher-quality providers. Example parameters to be updated and taken into account in setting the rating include consumers' overall ranking of the provider's engagement quality, the number of engagements made by this provider in the last 30 days or overall, the number of returning engagements as a fraction of all engagements for that provider, the number of redirected engagements from this provider to another, and the average turnaround time for messaging while not "out-of-office." In addition to the ratings each provider on the system has a Provider Statistic Manifest stating operational statistics that may interest consumers, such as that provider's availability for phone conferences over the last 30 days.

Consumers are asked to rank a provider at the end of the engagement as part of the process of disconnecting. To encourage consumers to provide such feedback, charges for the engagement continue to accrue until the consumer completes the ranking. Such a process helps encourage provider engagements to end with a ranking entry, promoting a higher quality of service to the brokerage's consumers.

The Provider Console

Providers interact with consumers through a provider console web page 350, shown in FIG. 10. This interface is similar to that used by the consumers. The provider console provides access to the various tools used by providers. A window shows a live image 352 of the consumer, with tools 354*a*, 354*b* to control or disable the video feed. A phone control 356 allows the provider to initiate a phone call with the consumer. A log of an ongoing chat 358 is displayed above an input 360 for the provider's next comment. Other tools are available in tabs 362 on the side, such as accesses to the terms of operation and the legal policies of the brokerage, such as disclaimers. State setting allows the providers to change his availability state between states such as off-line, on-line and out-of-office. Scheduling allows providers to update their availability calendar with future times they expect to be available on the system, which can in turn result in consumers seeing a "scheduled" state for such providers.

Messaging tools allow providers correspond with consumers in message-based engagements. The console also allows the provider to participate in chat engagements where the consumer and the provider communicate back-and-forth in real-time by typing, such as the chat 358 in FIG. 10. The brokerage allows a single provider to engage in more than one chat at a time to maximize his yield while consumers are typing their entries. The chat feature also allows the provider to forward specific lists of questions to further reduce the need for his time in acquiring information from the consumer at the beginning of an engagement. Tools available to assist the provider in chat or messaging may include a thread viewer, a clinical summary of the consumer, the consumer's engagement history, a communication timeline chart, and a library of built-in and self-produced message templates for quick response. Such templates may also include references, links, and embedded graphical educational content on prevalent topics. In some examples, the brokerage scans outbound messages for inappropriate language based on the sponsor's preferences.

The console allows the provider to hold a voice conference engagement with the consumer when the consumer is using either her computer or a telephone. The provider can use the console to redirect his end of the conference to a phone, for example, if bandwidth or other considerations indicate it or simply based on personal preference. The console also allows the provider to engage in video conferences with consumers. Audio may be served via the console or be may redirected to a telephone. To verify a provider's identity when using the telephone for a voice engagement, the system provides the provider with a PIN number through the provider console. When the provider calls into the system, or answers the phone when called by the system, the provider enters the PIN to confirm that the person on the phone is the same person who is logged into the console. This method is also used to leave secure voice message. When a provider wants to leave a message for a consumer, the provider tells the console and receive a PIN. The provider then receives a call from the system, enters the PIN, and leaves a message. The message is then delivered to the consumer with assurances that it was left by the provider.

At any time during an engagement, the provider may add notes to either the consumer engagement audit (consumer record) or to his own audit of the engagement. The audit trail allows the provider to review a complete audit of his consumer interactions via the console. This audit may include the content and timing of past engagements and related credits that the provider is due for the engagements.

In versions of the brokerage for fields, such as health care, that rely on detailed coding of work performed or analyses made, an encoder feature is provided throughout the engagement. The encoder allows the provider to add clinical codes describing the findings of the engagement. The codes can be used to further characterize the consumer as well as the basis for outbound communication to the follow-on points of care or interfaced clinical systems. The encoder can support, for example, coverage for disease, drug and procedure classifications.

The system may allow provider to provider interaction either in the context of a consumer (e.g., consultation or referral) or without a consumer context (e.g., provider forums, discussion boards, etc.). In a health care context, depending on the license of the provider to prescribe medications to an engaged consumer, the console allows the provider to use electronic prescription and refill services. Assuming it is authorized, the provider may instruct the system to forward transcripts of engagements or other information to another recipient outside the brokerage. Such exporting may include various modes of communication, such as electronic (e.g., fax, e-mail, SMS) or non-electronic (e.g., print, mail).

The provider is able to review his account status, system settings, and preferences. The provider can also access his profile and user satisfaction and statistics as they are available to consumers. The console also connects to financial services associated with the provider's participation in the brokerage. This includes status of charges, submission of plan claims (e.g., for CPT code 0074T for eVisits in a health care setting) and claim processing status. In some examples, depending on the mode of deployment of the brokerage from the health plan standpoint, real-time claim information may be available.

The brokerage offers providers the ability to redirect messages or requests for appointment to SMS-compatible cellular phones. In this mode, the provider associates a cell phone number with his account and establishes the type of information that the system can send to the mobile device. Such information may include engagement-related notifications as well as system-related notifications (e.g., an announcement about a high-traffic state asking providers to make themselves available and offering a higher fee to do so).

Open Access Forum

In some examples, the system includes an open forum that supports freeform engagements on different topics between all constituents. The open forum allows a consumer to anonymously post any of the issues identified by the consumer advisor or to manually post questions into a publicly-accessible forum. While the consumer posts his issues anonymously, responses or threads developing as other users provide answers or discuss the issues are forwarded to the consumer that posted the original issue. In some examples, the system monitors the identity of those who respond to a posting and differentially informs the consumer if a user known to be a provider posts a response. In some examples, the brokerage pays providers to post responses to entries they think are significant on the open forum. Unlike consumer entries, provider entries are identified and allow a consumer to start engagements with providers whose answers he finds informative or beneficial. The open forum also serves as a vehicle for providers to publicize themselves to consumers.

In some examples, a consumer posts the audit of one or more engagements onto the open forum for the benefit of other consumers. The brokerage strips any data that identifies the participants (i.e., it annonymizes the data) and offers the consumer the ability to review the anonymized data prior to posting it.

Sample Use Cases in the Medical Field

Generally Well Consumer

In one example, a consumer logs on to the system to explore a benefit that was promoted to him by his employer. The consumer is advised that use of the platform to increase her understanding of managing her health can be rewarded through an incentive program offered by the employer-provided health plan. The consumer advisor engages the consumer and undertakes a "no-reported-problem" assessment. At the end of the assessment, the consumer is surprised to find several areas where she can benefit from engagements. In this example, these areas include missing key cancer screening tests, improper gynecological follow-up, unattended family risk factors and a collection of lifestyle issues that both impose increasing risks and noticeably increase her stress and sleep quality issue levels. The brokerage lists and sequentially connects the consumer to an Ob/Gyn provider and a nurse coach, each already knowledgeable about the respective gaps identified. A summary report with a detailed appointment request is forwarded to the consumer's registered primary care physician to schedule the tests and referrals. The consumer receives educational material on the specific tests and risk factors that were identified.

Parents of a Newborn

In another example two parents are concerned with a rash developing on their child's left buttock. The parents are connected to a pediatric nurse who walks them through the characterization of the rash and determines it is a diaper-rash that can be managed by simple moisturizing ointment. The parents are advised that such a rash typically subsides in 2-3 days without treatment. In this example, the parents opt for further reassurance via pediatrician counseling. A connected pediatrician provides confirmation of the nurse's diagnosis and advise after reviewing the online notes. The parents follow-up with their regular pediatrician the following week, after the documentation of the event has been faxed to the pediatrician office.

A Chronic Diabetic Patient with Mobility Restrictions

In another example, a patient is a chronic overweight diabetic that is home bound. The patient develops pain in his shin above the ankle and engages the brokerage which directs him to an internal medicine specialist. The patient chooses to engage over the phone and connected with the specialist through the brokerage switchboard. The specialist questions the patient to identify a possible location of a developing leg ulcer and directs the patient to exercise extreme hygiene and heated compresses in the affected area. The specialist advises the patient not to wait for the pain to possibly subside. The patient's provider and his health plan's care manager are notified of the engagement and next-day admission for investigation and debridement is scheduled. The early stage ulcer identified by the specialist during the telephone engagement is managed, thus preventing a life-threatening deterioration of the patient's condition.

A 46 Year Old Banking Executive Female

In another example, a consumer logs on and takes the health risk assessment. The system recognizes that the consumer has questions about certain cosmetic procedures. The system formulates the questions that should be addressed and offers to connect the consumer with a plastic surgery resident. The consumer receives a list of the names and nature of the procedures she may want to explore for her cosmetic concerns. Links to reference information on each procedure are added to her record. Links that assist the consumer in comparing costs and possible providers in her geographical area who perform the procedures are also added.

Embodiments can be implemented in digital electronic circuitry, or in computer hardware, firmware, software, or in combinations thereof. Apparatus of the invention can be implemented in a computer program product tangibly embodied or stored in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD_ROM disks. Any of the foregoing can be supplemented by, or incorporated in, ASICs (application-specific integrated circuits).

Other embodiments are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A computer-implemented method comprises:
receiving in a computer, a request from a consumer of services to consult with a medical service provider having a medical service provider profile that satisfies at least some attributes associated with medical qualifications in a set of attributes that define a suitable medical service provider;
accessing a data repository that stores information pertaining to medical service providers, including present availability of the medical service providers for participating in a consultation;
determining in the computer, which of the medical service providers are presently available;
identifying in the computer, medical service providers satisfying at least some of the attributes in the set of attributes that define suitable medical service providers;
producing a set of available medical service providers that satisfy at least some of the attributes in the set of attributes to send to the consumer of services;
receiving a selection from the consumer of one of the medical service providers from the set of available medical service providers;
establishing an immediate, real-time communication channel between the consumer of services and the selected medical service provider;
identifying second available medical service providers of a second type of service provider satisfying at least some of the attributes associated with the medical specialty in the set of attributes;
receiving a selection from the consumer of one of the second available medical service providers; and
establishing a second immediate, real-time communication channel between the consumer of services and the second selected medical service provider, with the real-time communication channel and the second real-time communication channel being established concurrently or consecutively.

2. The method of claim 1 further comprises:
receiving an availability indication from a medical service provider; and
updating the data repository with the received availability indication from the medical service provider.

3. The method of claim 1 wherein the communication channel for whichever selected medical service provider is available first is established first.

4. The method of claim 1 wherein if the communication channel with the first selected medical service provider is established before the second communication channel, the method further comprises:
providing information describing an outcome of a communication established through the communication channel between the consumer of services and the first selected medical service provider to the second selected medical service provider in advance of establishing the second communication channel.

5. The method of claim 1 further comprising:
providing information describing an outcome of a communication established through the communication channel between the consumer of services and the selected medical service provider to a second medical service provider associated with the consumer of services.

6. The method of claim 1 wherein establishing the communication channel comprises:
identifying a communication method for contacting the consumer of services; and
instructing the selected medical service provider to initiate a communication using the identified method.

7. The method of claim 1 wherein establishing the communication channel comprises:
establishing a first communication channel with the consumer of services;
establishing a second communication channel with the selected medical service provider; and
connecting the first and second communication channels.

8. The method of claim 1 wherein
establishing a communication channel between the consumer of services and the selected medical service provider includes receiving an indication that the selected medical service provider has initiated a first communication channel.

9. The method of claim 8 further comprises:
establishing a second communication channel with the consumer of services; and
connecting the first and second communication channels.

10. A computer-implemented method comprises:
accessing a data repository that stores information pertaining to medical service providers, including present availability of the medical service providers for participating in a consultation;
receiving in a computer, indications that members of a pool of medical service providers have become presently available;
receiving in the computer, a request from a consumer of services to consult with a medical service provider;
identifying in the computer, an available member of the pool; and
establishing a real-time communication channel between the consumer of services and the identified member of the pool.

11. The method of claim 10 wherein:
the request includes an identification of a time in the future; and
identifying the member of the pool and establishing the communication channel take place at the identified time.

12. A computer implemented method comprises:
receiving in a computer, a request from a patient for an on-demand, real-time consultation with a physician;
accessing a data repository that stores information pertaining to physicians, including present availability of the physicians for participating in a consultation;
determining in the computer, which of the physicians are presently available;
identifying in the computer, at least one available physician with whom the patient should consult;
receiving a selection from the patient of one of the identified physicians; and
activating a real-time communication channel between the patient and the selected physician.

13. The method of claim 12 in which identifying the available physician comprises:
identifying at least one type of physician with whom the patient should consult;
identifying a set of physicians of the identified type;
determining the current availability of physicians in the identified set; and
identifying an available physician in the identified set.

14. The method of claim 13 wherein:
the patient is associated with a primary physician, and
identifying the set of physicians includes identifying physicians other than the patient's primary physician.

15. The method of claim 14 further comprising:
providing information describing an outcome of a consultation established through the real-time communication channel to the patient's primary physician.

16. A computer implemented method comprises:
sending a request from a patient for an on-demand, real-time consultation with a physician;
accessing a data repository that stores information pertaining to physicians, including present availability of the physicians for participating in a consultation;
determining in the computer, which of the physicians are presently available;
receiving a message identifying at least one available physician with whom the patient should consult;
receiving a selection from the patient of one of the identified physicians; and
establishing a communication channel between the patient and the selected physician.

17. A computer program product residing on a computer readable medium for providing broker services to consumers and medical service providers, the computer program product comprising instructions for causing a computer to:
receive a request from a consumer of services to consult with a medical service provider having a medical service provider profile that satisfies at least some attributes associated with medical qualifications in a set of attributes that define a suitable service provider;
access a data repository that stores information pertaining to medical service providers, including present availability of the medical service providers for participating in a consultation;
determine in the computer, which of the medical service providers are presently available;
identify medical service providers that satisfy at least some of the attributes in the set of attributes that define a suitable medical service provider;
produce a set of available medical service providers that satisfy at least some of the attributes in the set of attributes to send to the consumer of services;
receive a selection from the consumer of one of the medical service providers from the set of available service providers; and
establish a communication channel between the consumer of services and the medical selected service provider.

18. The computer program product of claim 17 further comprising instructions to:
monitor availability of the selected medical service provider.

19. The computer program product of claim 17 wherein the instructions to identify medical service providers include instructions to:
determine whether the medical service provider are available.

20. The computer program product of claim 17 further comprising instructions to:
receive an availability indication from a medical service provider; and
update the data repository with the received availability indication from the medical service provider.

21. The computer program product of claim 17 further comprising instructions to:
provide information describing an outcome of a communication established through the communication channel between the consumer of services and the selected medical service provider to a second medical service provider associated with the consumer of services.

22. The computer program product of claim 17 wherein the instructions to establish the communication channel include instructions to:
   establish a first communication channel with the consumer of services;
   establish a second communication channel with the selected medical service provider; and
   connect the first and second communication channels.

23. A computer program product residing on a computer readable medium for providing broker services to consumers and service providers, the computer program product comprising instructions for causing a computer to:
   access a data repository that stores information pertaining to medical service providers, including present availability of the medical service providers for participating in a consultation;
   receive indications that members of a pool of medical service providers have become presently available;
   receive a request from a consumer of services to consult with a medical service provider;
   identify an available member of the pool; and
   establish a real-time communication channel between the consumer of services and the identified member of the pool.

24. An apparatus comprising:
   a processor; and
   a computer program product residing on a computer readable medium for providing broker services to consumers and service providers, the computer program product comprising instructions for causing the processor to:
   receive a request from a consumer of services to consult with a medical service provider having a medical service provider profile that satisfies at least some attributes associated with medical qualifications in a set of attributes that define a suitable service provider;
   access a data repository that stores information pertaining to medical service providers, including present availability of the medical service providers for participating in a consultation;
   determine in the computer, which of the medical service providers are presently available;
   identify medical service providers that satisfy at least some of the attributes in the set of attributes that define a suitable medical service provider;
   produce a set of available medical service providers that satisfy at least some of the attributes in the set of attributes to send to the consumer of services;
   receive a selection from the consumer of one of the medical service providers from the set of available medical service providers; and
   establish a communication channel between the consumer of services and the selected medical service provider.

25. The apparatus of claim 24, the computer program product further comprising instructions to:
   monitor availability of the selected medical service provider.

26. The apparatus of claim 24 wherein the instructions to identify medical service providers include instructions to:
   determine whether the medical service providers are available.

27. The apparatus of claim 24, the computer program product further comprising instructions to:
   receive an availability indication from a medical service provider; and
   update the data repository with the received availability indication from the medical service provider.

28. The apparatus of claim 24, the computer program product further comprising instructions to:
   provide information describing an outcome of a communication established through the communication channel between the consumer of services and the selected medical service provider to a second medical service provider associated with the consumer of services.

29. The apparatus of claim 24 wherein the instructions to establish the communication channel include instructions to:
   establish a first communication channel with the consumer of services;
   establish a second communication channel with the identified medical service provider; and
   connect the first and second communication channels.

30. An apparatus comprising:
   a processor; and
   a computer program product residing on a computer readable medium for providing broker services to consumers and service providers, the computer program product comprising instructions for causing the processor to:
   access a data repository that stores information pertaining to medical service providers, including present availability of the medical service providers for participating in a consultation;
   receive indications that members of a pool of medical service providers have become presently available;
   receive a request from a consumer of services to consult with a medical service provider;
   identify an available member of the pool; and
   establish a real-time communication channel between the consumer of services and the identified member of the pool.

* * * * *

UNITED STATES PATENT AND TRADEMARK OFFICE
CERTIFICATE OF CORRECTION

PATENT NO. : 7,590,550 B2
APPLICATION NO. : 11/763680
DATED : September 15, 2009
INVENTOR(S) : Roy Schoenberg It is certified that error appears in the above-identified patent and that said Letters Patent is hereby corrected as shown below:

Title Pg, Item (56) References Cited, please delete "1/2006" and insert --1/2009--, therefor.

Col. 1, line 7 of the Specification, please delete "Application" and insert --Applications--, therefor.

Signed and Sealed this

Eighth Day of December, 2009

David J. Kappos
*Director of the United States Patent and Trademark Office*